US012569164B2

(12) United States Patent
O'Brien et al.

(10) Patent No.: US 12,569,164 B2
(45) Date of Patent: Mar. 10, 2026

(54) DEVICE FOR MEASURING A PERSON'S VENTILATION INCLUDING OXYGEN-CONSUMPTION

(71) Applicant: VO2 MASTER HEALTH SENSORS INC., Vernon (CA)

(72) Inventors: Peter O'Brien, Vernon (CA); Kyle Halliday, Nanaimo (CA)

(73) Assignee: VO2 MASTER HEALTH SENSORS INC., Vernon (CA)

( * ) Notice: Subject to any disclaimer, the term of this patent is extended or adjusted under 35 U.S.C. 154(b) by 698 days.

(21) Appl. No.: 16/970,325

(22) PCT Filed: Oct. 18, 2018

(86) PCT No.: PCT/CA2018/051314
§ 371 (c)(1),
(2) Date: Aug. 14, 2020

(87) PCT Pub. No.: WO2019/173894
PCT Pub. Date: Sep. 19, 2019

(65) Prior Publication Data
US 2021/0076979 A1      Mar. 18, 2021

Related U.S. Application Data

(60) Provisional application No. 62/643,744, filed on Mar. 15, 2018.

(51) Int. Cl.
*A61B 5/083*        (2006.01)
*A61B 5/00*         (2006.01)
(Continued)

(52) U.S. Cl.
CPC ............ *A61B 5/0833* (2013.01); *A61B 5/087* (2013.01); *A61B 5/097* (2013.01); *A61B 5/6803* (2013.01);
(Continued)

(58) Field of Classification Search
CPC ....... A61B 5/0833; A61B 5/087; A61B 5/097; A61B 5/6803; A61B 2560/04;
(Continued)

(56) References Cited

U.S. PATENT DOCUMENTS

| | | | |
|---|---|---|---|
| 3,661,528 A | 5/1972 | Falk | |
| 3,735,752 A | 5/1973 | Rodder | |

(Continued)

FOREIGN PATENT DOCUMENTS

| | | |
|---|---|---|
| CA | 2430613 | 11/2004 |
| EP | 0794806 | 2/1996 |

(Continued)

OTHER PUBLICATIONS

"Venturi", Merriam-Webster Online and found on the WayBackMachine archived page dated Feb. 19, 2010: https://web.archive.org/web/20100219215417/https://www.merriam-webster.com/dictionary/venturi.

(Continued)

*Primary Examiner* — Jason M Sims
*Assistant Examiner* — Kyle W. Kretzer
(74) *Attorney, Agent, or Firm* — Nicholas Garner; Oyen Wiggs Green & Mutala LLP

(57) ABSTRACT

The present invention relates to a device for measuring a person's ventilation. The device includes a conduit with an exhaled-air receiving portion and an inhaled-air receiving portion. The device includes pressure and oxygen sensor sampling ports. The sampling ports are in fluid communication with the conduit. The device includes a deflector disposed within the conduit. The deflector is configured to deflect air exhaled into the exhaled-air receiving portion of the conduit away from the sensor ports.

29 Claims, 23 Drawing Sheets

(51) Int. Cl.
   *A61B 5/087*       (2006.01)
   *A61B 5/097*       (2006.01)

(52) U.S. Cl.
   CPC ... *A61B 2560/04* (2013.01); *A61B 2562/0247*
                         (2013.01)

(58) Field of Classification Search
   CPC ............ A61B 2560/0247; A61B 5/083; A61B
                        5/6814; A61B 5/682
   See application file for complete search history.

(56) References Cited

U.S. PATENT DOCUMENTS

| | | | |
|---|---|---|---|
| 3,924,467 | A | 12/1975 | Takamura et al. |
| 4,142,407 | A | 3/1979 | Kuroiwa et al. |
| 4,197,857 | A | 4/1980 | Osborn |
| 4,292,978 | A | 10/1981 | Guth |
| 4,297,871 | A | 11/1981 | Wright et al. |
| 4,404,859 | A | 9/1983 | Ohsawa et al. |
| 4,440,177 | A | 4/1984 | Anderson et al. |
| 4,620,248 | A | 10/1986 | Gitzendanner |
| 4,658,832 | A | 4/1987 | Brugnoli |
| 4,705,543 | A | 11/1987 | Kertzman |
| 4,736,750 | A | 4/1988 | Valdespino et al. |
| 4,808,201 | A | 2/1989 | Kertzman |
| 5,072,737 | A | 12/1991 | Goulding |
| 5,184,501 | A | 2/1993 | Lewis et al. |
| 5,363,857 | A | 11/1994 | Howard |
| 5,705,735 | A | 1/1998 | Acorn |
| 5,857,461 | A * | 1/1999 | Levitsky ................ A61B 5/083 |
| | | | 128/207.14 |
| 5,913,249 | A | 6/1999 | Weckstrom |
| 5,957,127 | A | 9/1999 | Yamamori et al. |
| 6,206,837 | B1 | 3/2001 | Brugnoli |
| 6,435,183 | B1 | 8/2002 | Farman |
| 6,572,561 | B2 | 6/2003 | Mault |
| 6,612,306 | B1 | 9/2003 | Mault |
| 6,629,933 | B1 | 10/2003 | Lindner |
| 6,629,934 | B2 | 10/2003 | Mault et al. |
| 6,815,211 | B1 | 11/2004 | Blazewicz et al. |
| 6,899,683 | B2 | 5/2005 | Mault et al. |
| 6,955,650 | B2 | 10/2005 | Mault et al. |
| 6,983,663 | B2 | 1/2006 | Fathollahzadeh |
| 7,108,659 | B2 * | 9/2006 | Ross .................... A61B 5/6814 |
| | | | 600/529 |
| 7,618,235 | B2 | 11/2009 | Sacco |
| 7,621,271 | B2 | 11/2009 | Brugnoli |
| RE41,332 | E | 5/2010 | Binder |
| 7,730,793 | B2 | 6/2010 | Speldrich |
| 8,002,712 | B2 | 8/2011 | Meka et al. |
| 8,197,417 | B2 | 6/2012 | Howard et al. |
| 8,684,900 | B2 | 4/2014 | Tran |
| 9,498,150 | B2 * | 11/2016 | Colman ................. A61B 5/097 |
| 9,706,965 | B2 | 7/2017 | Colman et al. |
| 10,271,766 | B1 | 4/2019 | Parker, Jr. et al. |
| 10,381,849 | B2 | 8/2019 | Wing et al. |
| 11,284,814 | B2 | 3/2022 | O'Brien et al. |
| 2002/0100474 | A1 | 8/2002 | Kellner et al. |
| 2003/0028120 | A1 * | 2/2003 | Mault ................. G01N 33/497 |
| | | | 600/531 |
| 2003/0065274 | A1 * | 4/2003 | Mault ................... A61B 5/087 |
| | | | 600/531 |
| 2003/0208132 | A1 | 11/2003 | Baddour |
| 2003/0208133 | A1 | 11/2003 | Mault |
| 2004/0094155 | A1 | 5/2004 | Castor et al. |
| 2004/0186390 | A1 | 9/2004 | Ross et al. |
| 2005/0004488 | A1 | 1/2005 | Hoppe et al. |
| 2005/0154386 | A1 | 7/2005 | West et al. |
| 2007/0093725 | A1 | 4/2007 | Shaw |

| | | | |
|---|---|---|---|
| 2007/0107728 | A1 * | 5/2007 | Ricciardelli .......... A61B 5/083 |
| | | | 128/204.22 |
| 2010/0036272 | A1 | 2/2010 | Mace et al. |
| 2011/0319783 | A1 | 12/2011 | Lindholt et al. |
| 2012/0234696 | A1 | 9/2012 | Mosley et al. |
| 2013/0267803 | A1 | 10/2013 | Kramer |
| 2013/0331726 | A1 | 12/2013 | Weber |
| 2014/0024960 | A1 | 1/2014 | Smith et al. |
| 2014/0276171 | A1 * | 9/2014 | Hestness ................ A61B 5/097 |
| | | | 600/249 |
| 2014/0364758 | A1 | 12/2014 | Schindhelm et al. |
| 2014/0378792 | A1 | 12/2014 | Krimsky et al. |
| 2015/0083121 | A1 | 3/2015 | Fisher et al. |
| 2015/0119744 | A1 * | 4/2015 | Lawson ................ G01F 15/028 |
| | | | 600/539 |
| 2017/0049978 | A1 | 2/2017 | Berg et al. |
| 2017/0055875 | A1 | 3/2017 | Candell et al. |
| 2017/0119279 | A1 | 5/2017 | Ahmad |
| 2017/0135605 | A1 * | 5/2017 | Sandholt ................ A61B 5/087 |
| 2017/0173262 | A1 | 6/2017 | Veltz |
| 2018/0153440 | A1 | 6/2018 | Lee et al. |
| 2019/0110714 | A1 | 4/2019 | O'Brien et al. |
| 2019/0120821 | A1 | 4/2019 | Atsalakis |
| 2020/0022618 | A1 * | 1/2020 | Mcclung .............. A61B 5/0833 |
| 2020/0121222 | A1 | 4/2020 | Becker et al. |
| 2021/0378546 | A1 | 12/2021 | Xian et al. |
| 2022/0031987 | A1 | 2/2022 | Wysoski |

FOREIGN PATENT DOCUMENTS

| | | |
|---|---|---|
| EP | 0911051 | 4/1999 |
| EP | 2606820 A1 | 6/2013 |
| EP | 2670491 A2 | 12/2013 |
| EP | 2769673 A1 | 8/2014 |
| EP | 2259723 | 5/2016 |
| EP | 3028627 B1 | 7/2016 |
| WO | 9118279 | 11/1991 |
| WO | 0028881 | 5/2000 |
| WO | 2001008554 | 2/2001 |
| WO | 03010496 | 2/2003 |
| WO | 2004041084 A1 | 5/2004 |
| WO | 2008060165 | 5/2008 |
| WO | 2008064062 | 5/2008 |
| WO | 2015127994 A1 | 9/2015 |
| WO | 2016138380 A1 | 9/2016 |
| WO | 2017177340 | 10/2017 |
| WO | 2019173894 | 9/2019 |
| WO | 2020076855 A1 | 4/2020 |

OTHER PUBLICATIONS

"Venturi effect", as set out in the archived version of the Wikipedia page for the same dated Jan. 6, 2015: https://en.wikipedia.org/w/index.php?title=Venturi_effect&oldid=641227804.

International Search Report for PCT/CA2017/050467, dated Aug. 17, 2017.

Written Opinion for PCT/CA2017/050467, dated Aug. 17, 2017.

"Series LX-Valve" product specification, from Parker Hannifin Corp., dated Mar. 2016.

International Search Report and Written Opinion for PCT/CA2018/051314, dated Jan. 8, 2019.

European Search Report dated Jan. 17, 2020 for EP 17 78 1693.

J. C. T. Pepperell et al. "P139 The use of venturi masks with oxygen concentrators", Thorax, vol. 66, No. Suppl. 4, Dec. 1, 2011, pp. A123-A124, XP055649271, GB, ISSN: 0040-6376, DOI: 10.1136/thoraxjnl-2011-201054c.139.

European Search Report for European Patent Application No. 23186942.1, completed Oct. 27, 2023 (mailed Nov. 7, 2023).

Supplementary European Search Report dated Sep. 25, 2024 issued on European Patent Application No. EP 21878818.

* cited by examiner

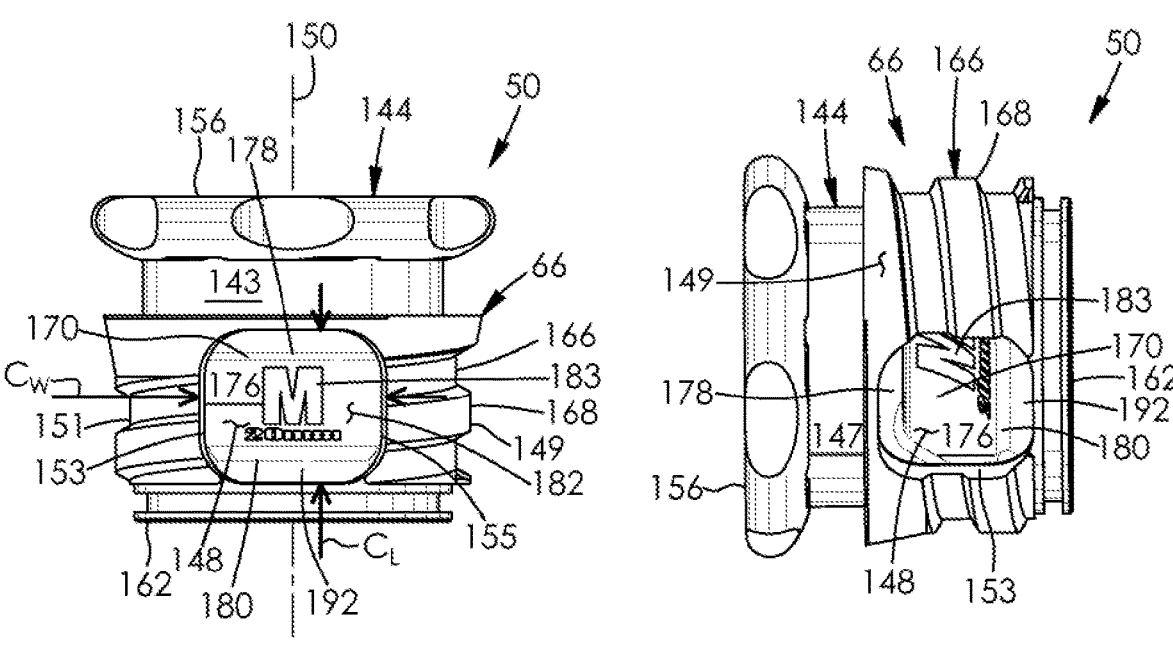
FIG. 16          FIG. 17
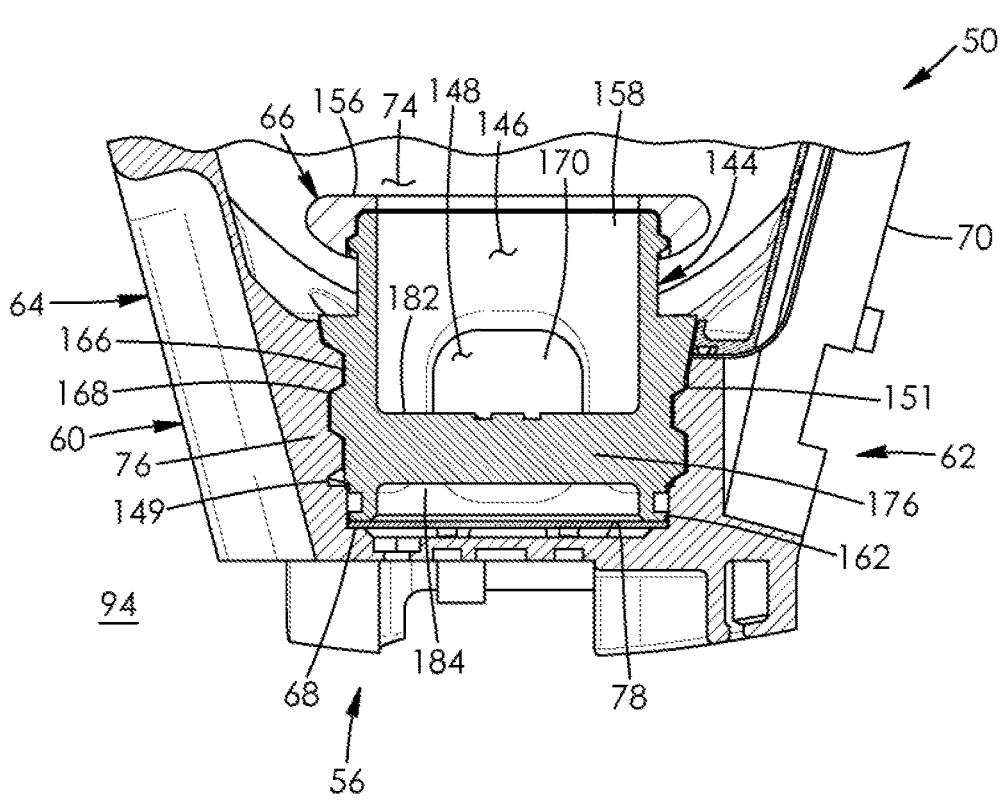
FIG. 18

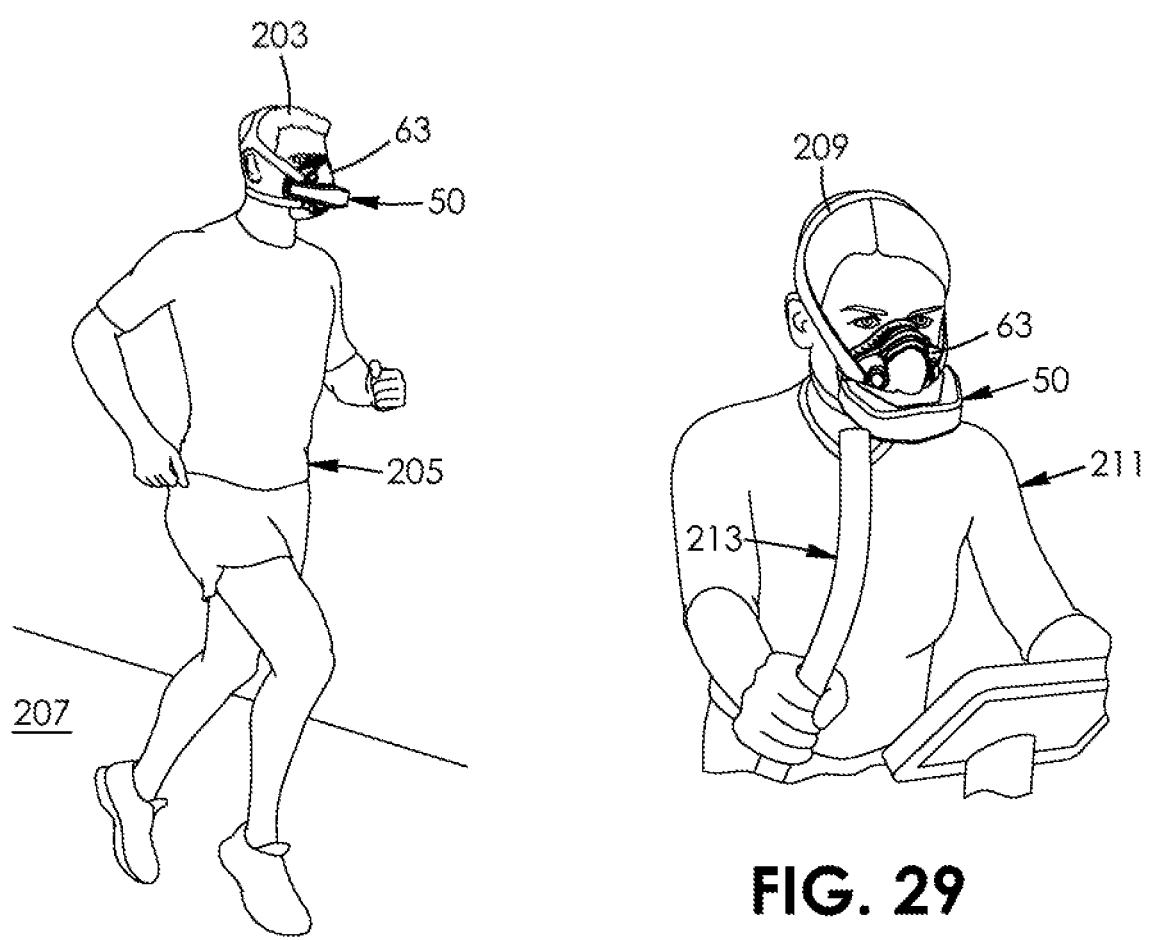
FIG. 29
FIG. 28
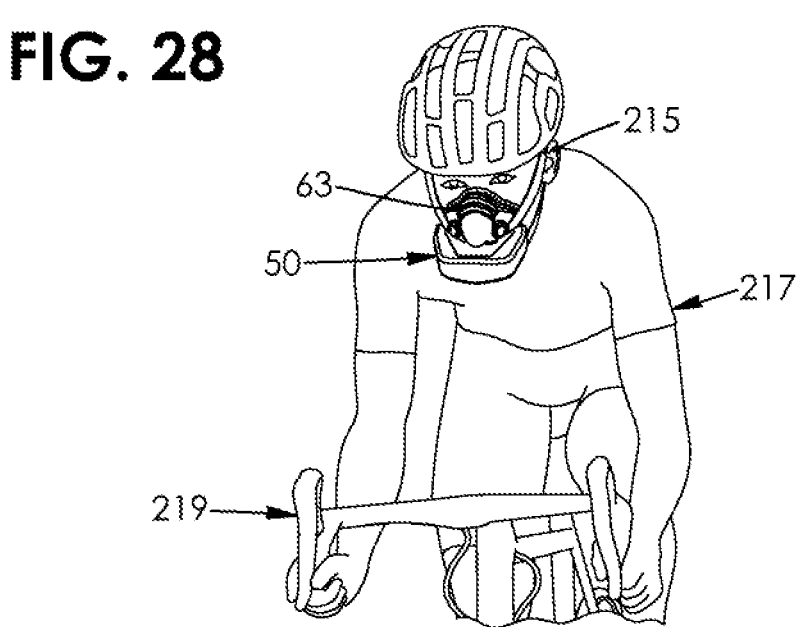
FIG. 30

DEVICE FOR MEASURING A PERSON'S VENTILATION INCLUDING OXYGEN-CONSUMPTION

CROSS REFERENCE TO RELATED APPLICATION

This application is a non-provisional of U.S. patent application No. 62/643,744 filed in the United States Patent and Trademark Office on Mar. 15, 2018, the disclosure of which is incorporated herein by reference and priority to which is claimed.

BACKGROUND OF THE INVENTION

Field of the Invention

The present invention relates to a measuring device. In particular, the invention relates to a device for measuring a person's ventilation, including oxygen-consumption.

Description of the Related Art

A conventional oxygen consumption ("VO2") monitoring device may use a pump to draw air away from the user's air stream. The device may further include a desiccation system, a relatively large mixing chamber, and an oxygen sensor. It may be undesirable for the user to have attached to their face the entirety of a conventional VO2 monitor due to the excessive vibration, weight, and noise. To mitigate against this, such assemblies may be split into two parts: a face mask for flow measurement, and an external box located either in a backpack or a table-top unit with a tube connecting the two parts. The mixing chamber is typically needed to stabilize a gas sample prior to analysis, and/or to remove physical vibration caused by a pump.

Such assemblies may thus require a relatively large number of parts and may be bulky as well as expensive.

There may accordingly be a need for an improved device that overcomes the above and other disadvantages of the known prior art.

BRIEF SUMMARY OF INVENTION

The present invention provides, and it is an object to provide, an improved device for measuring a person's ventilation, including oxygen-consumption.

There is accordingly provided a device for measuring a person's ventilation. The device includes a conduit with an exhaled-air receiving portion and an inhaled-air receiving portion. The device includes pressure and oxygen sensor sampling ports. The sampling ports are in fluid communication with the conduit. The device includes a deflector disposed within the conduit. The deflector is configured to deflect air exhaled into the exhaled-air receiving portion of the conduit away from the sensor ports.

There is also provided a device for measuring a person's oxygen-consumption. The device includes a conduit. The conduit has a first end through which the person's exhalations enter into the device and a second end through which air to be inhaled enters into the device. The device includes a divider positioned within the conduit. The divider at least in part forms a primary channel through which air primarily flows between said ends of the conduit. The divider at least in part forms a second channel through which a reduced amount of said air flows between the ends of the conduit. The device includes an oxygen sensor in fluid communication the second channel. The device includes a flow sensor which is also in fluid communication with both the second channel and ambient.

There is further provided a device for measuring a person's oxygen-consumption. The device includes a conduit. The conduit has a first end through which exhalations enter into the device in a first direction and a second end through which air to be inhaled enters into the device in a second direction which is perpendicular to the first direction. The device includes a deflector positioned within the conduit. The deflector is configured to direct air from the first end to the second end of the conduit and direct air from the second end to the first end of the conduit. The device includes an oxygen sensor sampling port and a flow sensor sampling port positioned within the conduit. The deflector is positioned between the sampling ports and the first end of the conduit.

There is yet further provided a kit for measuring a user's oxygen consumption. The kit includes a plurality of conduits. Each of the conduits includes an exhaled-air receiving portion and an inhaled-air receiving portion. The conduits are of different shapes tailored to different desired test conditions and criteria. The kit includes a sensor assembly to which respective ones of the conduits are selectively connectable. The sensor assembly includes pressure and oxygen sensor sampling ports. The sampling ports are in fluid communication with a user-selected said conduit so connected to the sensor assembly. The kit includes a plurality of deflectors, each disposed within a respective one of the conduits and configured to deflect air exhaled into the exhaled-air receiving portion of the user-selected said conduit so connected to the sensor assembly away from the sensor ports.

BRIEF DESCRIPTION OF DRAWINGS

The invention will be more readily understood from the following description of preferred embodiments thereof given, by way of example only, with reference to the accompanying drawings, in which:

FIG. 16 is a bottom plan view thereof;

FIG. 17 is a bottom, right side perspective view of thereof;

FIG. 18 is a sectional, fragmentary view taken along line 18-18 of the deflector assembly and inner subassembly of the sensor assembly of FIG. 9;

FIG. 28 is a perspective view of the face mask and ventilation measuring device of FIG. 1 shown in use and worn by a person who is running;

FIG. 29 is a perspective, fragmentary view of the face mask and ventilation measuring device of FIG. 1 shown in use and worn by a person who is exercising on an elliptical machine;

FIG. 30 is a perspective, fragmentary view of the face mask and ventilation measuring device of FIG. 1 shown in use and worn by a person who is exercising via a road bike;

DESCRIPTION OF THE PREFERRED EMBODIMENTS

Figure 1:
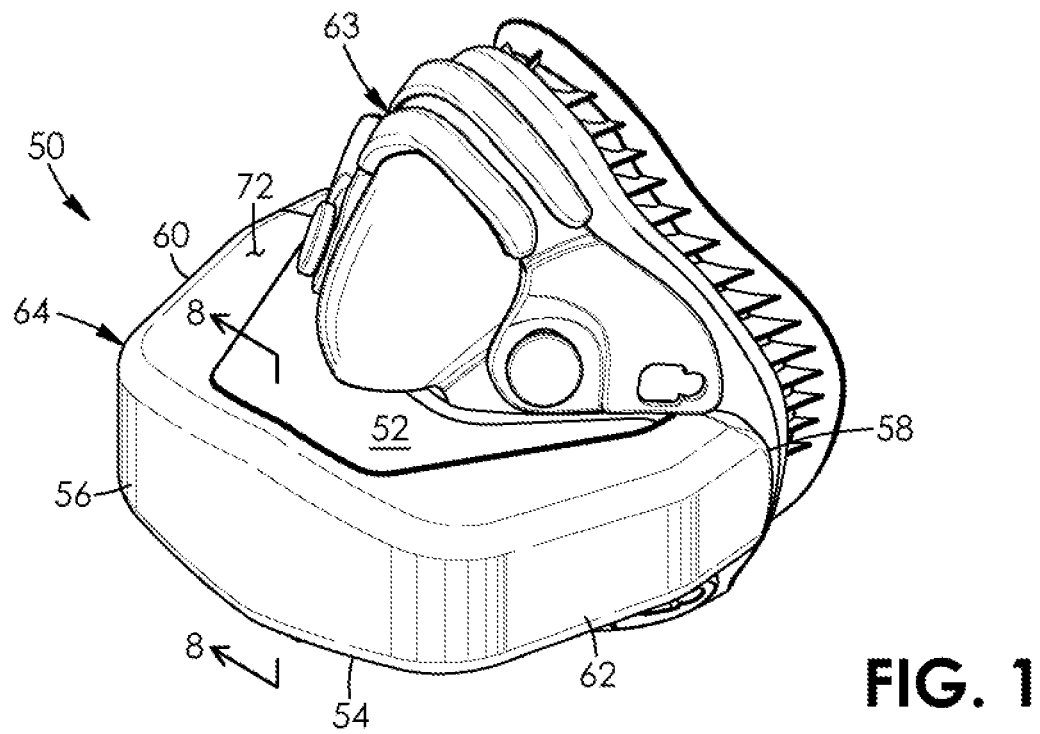
FIG. 1 is a front, top, right side perspective view of a face mask with a ventilation measuring device coupled thereto, the measuring device being according to a first embodiment.

Referring to the drawings and first to FIG. 1, there is provided a device for measuring a person's ventilation, namely a ventilation measuring device 50. The device measures various ventilation-related data including oxygen-consumption and the device may thus also be referred to as an oxygen-consumption measuring device. The device 50 has a top 52, a bottom 54, a front 56, a rear 58 and a pair of opposite sides 60 and 62. The sides of the device 50 extend between the top and bottom of the device, and between the front and rear of the device. The front 56 and rear 58 of the device extend between the top and bottom of the device.

The sides 60 and 62 and rear 58 of the device 50 are connectable to a breath-receiving member, in this example a face mask 63 shaped to cover a person's mouth and nose. In this example, the face mask is an off-the-shelf component of a 7450 V2-type which may be purchased at Hans Rudolf, Inc., having an address of 8325 Cole Parkway Shawnee, Kansas, 66227. United States of America. However, this type of face mask is not strictly required and other types face masks or mouth and/or nose engagement mechanisms may be used in other embodiments, such as a swimming snorkel mouthpiece with a nose clamp, for example.

Figure 3:
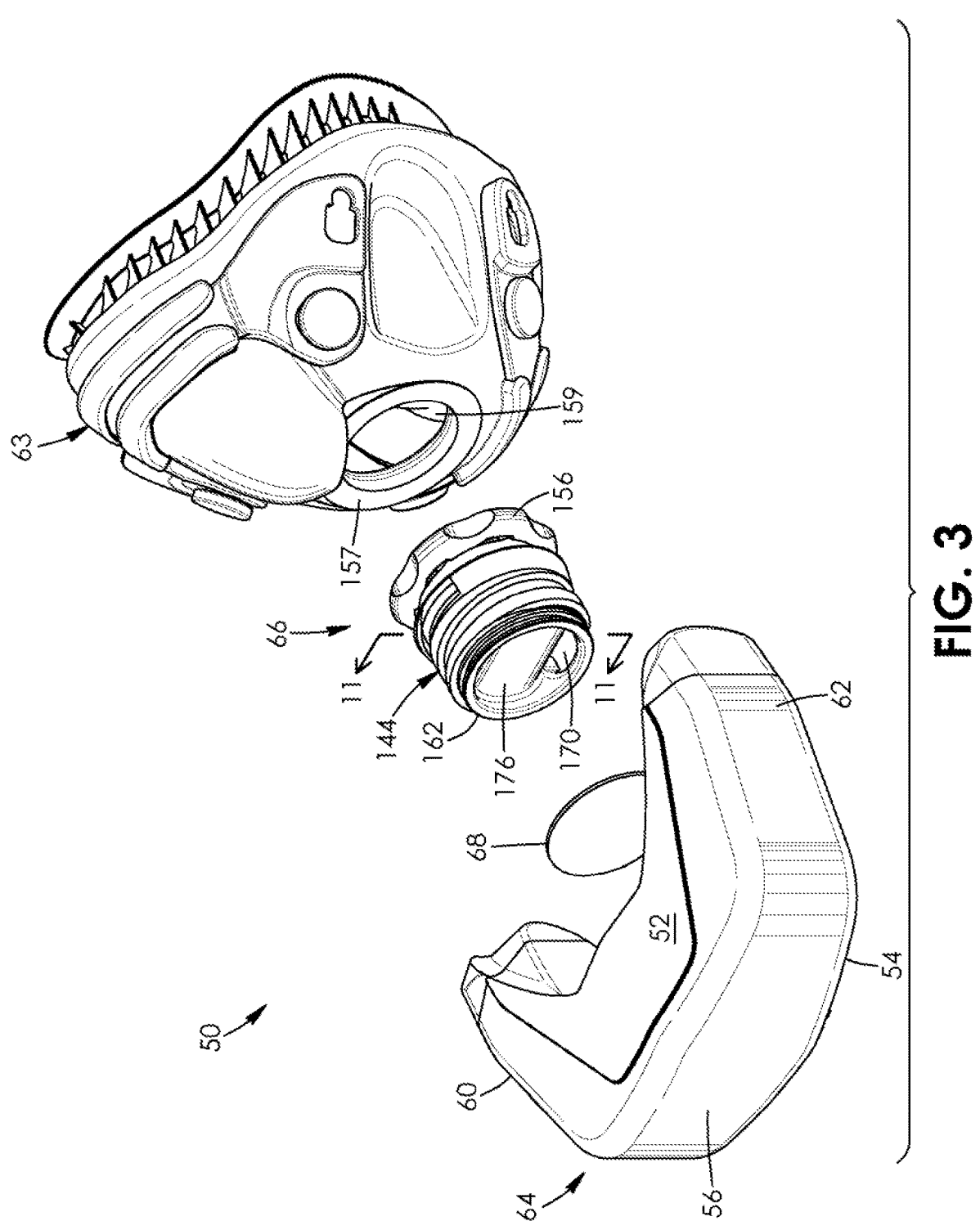
FIG. 3 is an exploded, top, right side perspective view of the measuring device and face mask of FIG. 1, the device including a sensor assembly, a filter, and a deflector assembly shaped to selectively couple to the deflector assembly, and the sensor assembly comprising an inner subassembly and an outer shell extending about the inner subassembly.

As seen in FIG. 3, the device 50 includes a sensor assembly 64, a deflector assembly 66 threadably connectable to the sensor assembly, and a filter 68 interposable between the sensor assembly and deflector assembly. The filter in this example is an off-the-shelf product in this example that may be purchased at Superior Felt & Filter, having an address of 1150 Ridgeview Drive, McHenry, Illinois, 60050, United States of America, for instance. However, this is not strictly required and other types of filters may be used.

Figures 4, 5, 6:
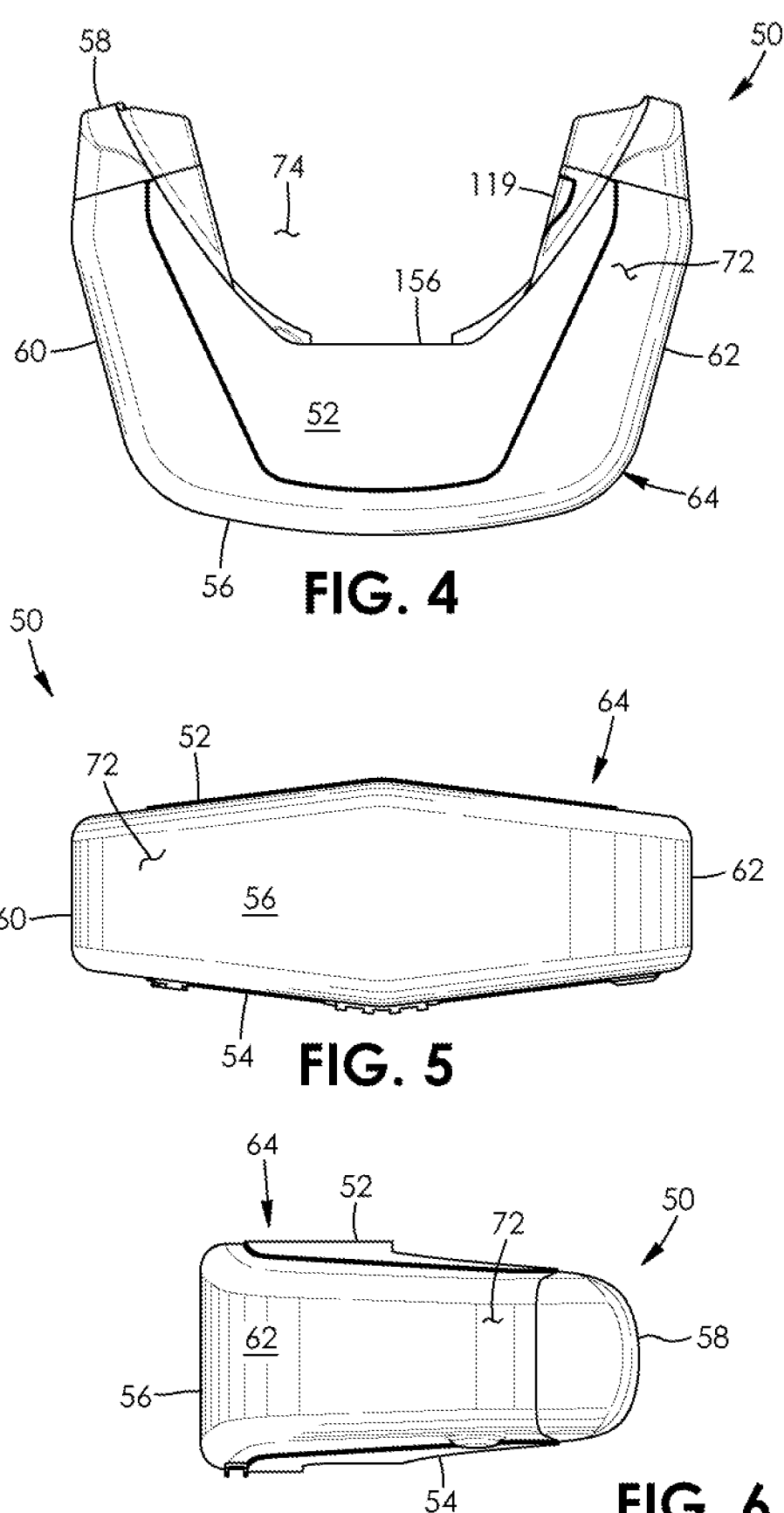
FIG. 4 is a top plan view of the measuring device of FIG. 1, with the face mask and deflector assembly not shown.
FIG. 5 is a front elevational view thereof
FIG. 6 is a right side elevational view thereof.

As seen in FIG. 4, the sensor assembly 64 is u-shaped in top and bottom profile, with a centrally-positioned recessed portion 74 extending from the rear 58 towards the front 56 of the device 50 in this example. As seen in FIG. 5, the sensor assembly is an elongated hexagon in front profile in this example.

Figures 7, 8:
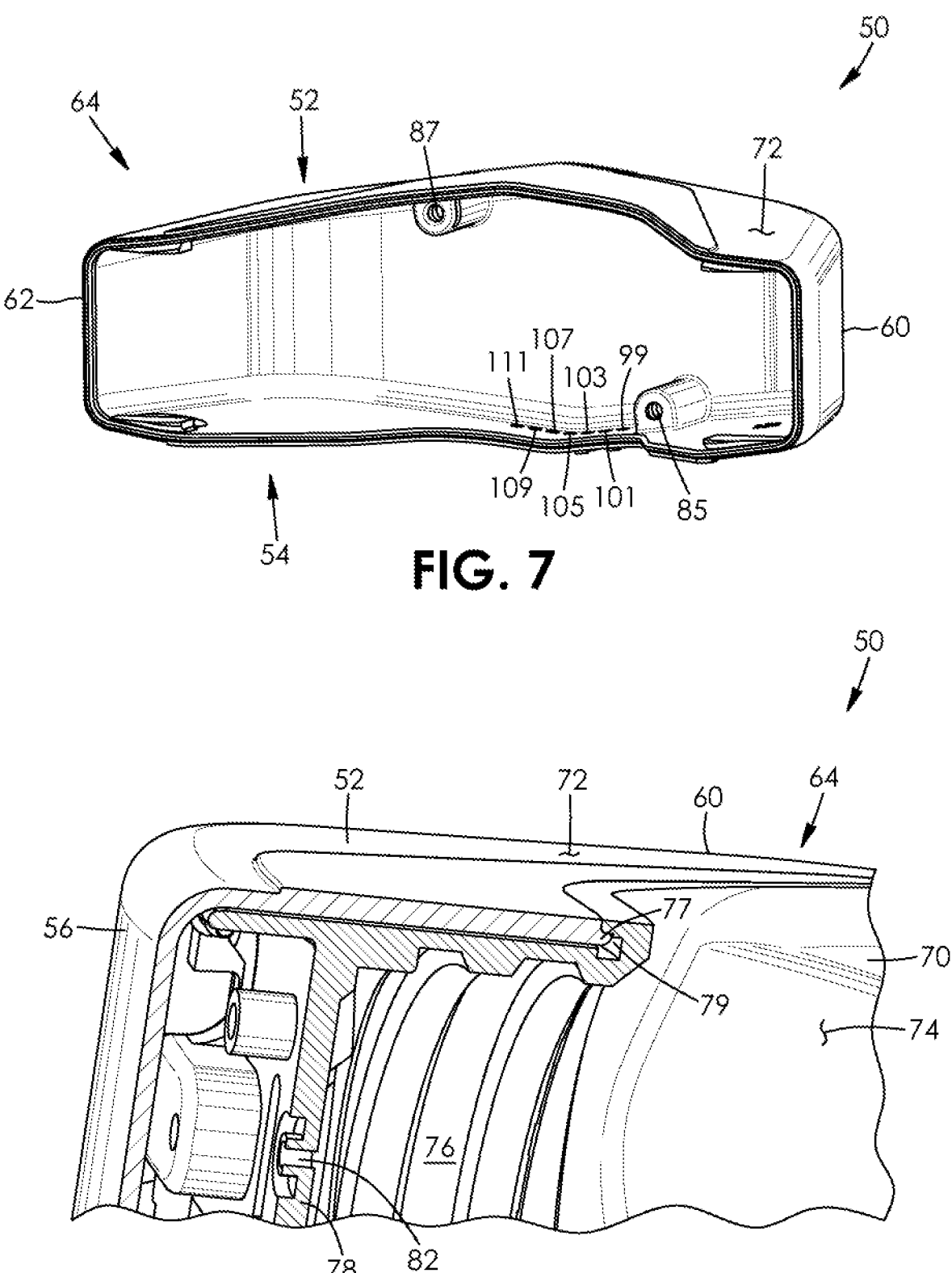
FIG. 7 is a rear perspective view of the outer shell of the sensor assembly of FIG. 3, with the inner subassembly of the sensor assembly and the deflector assembly not being shown.
FIG. 8 is an enlarged, sectional, fragmentary view taken along lines 8-8 of the measuring device of FIG. 1, with the deflector assembly thereof not shown coupled to the sensor assembly thereof.
Figures 9, 10:
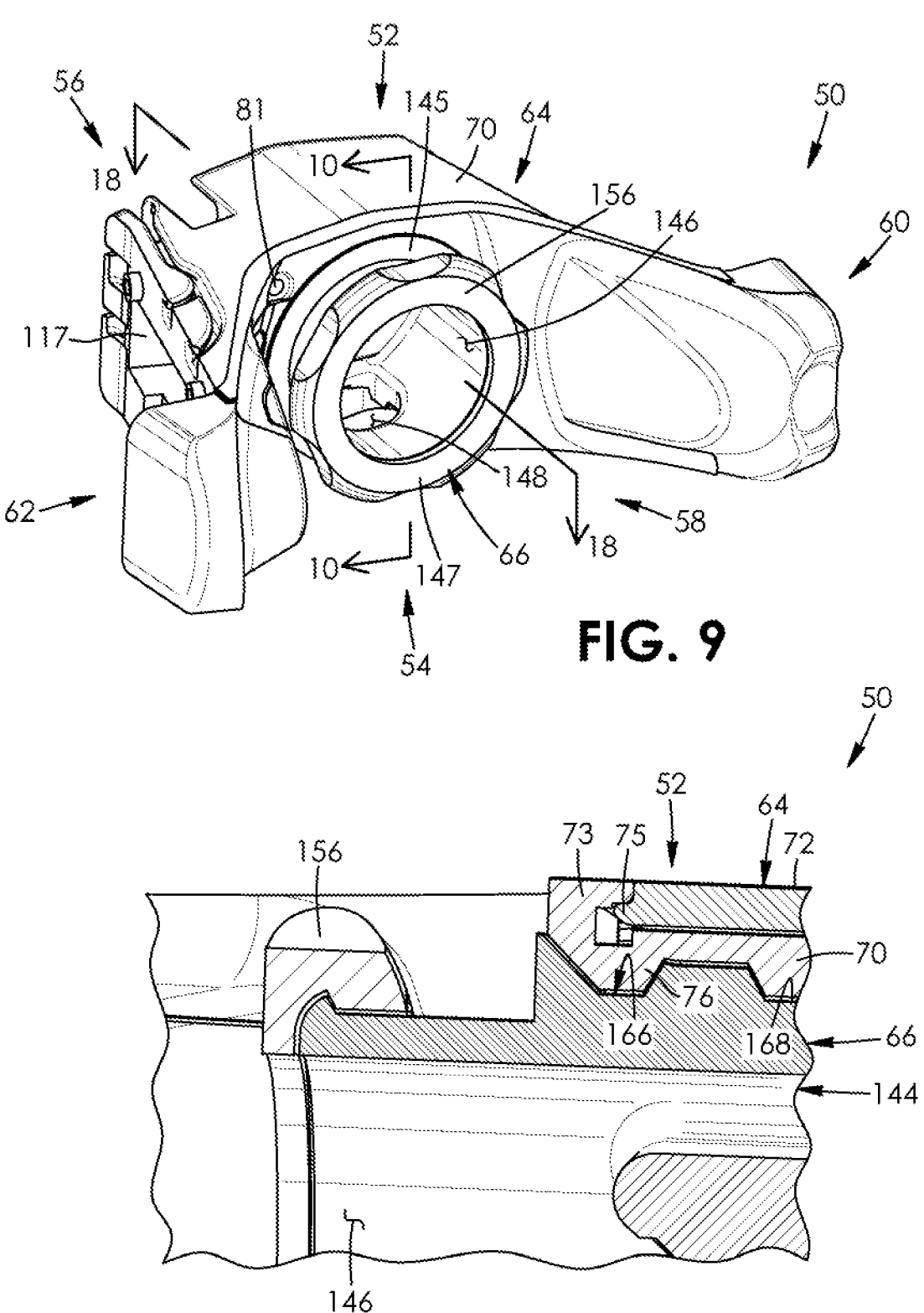
FIG. 9 is a rear, right side of the deflector assembly of FIG. 3 coupled to the inner subassembly of the sensor assembly of FIG. 3, with the outer shell of the sensor assembly not shown.
FIG. 10 is an enlarged, sectional, fragmentary view taken along lines 10-10 of the outer shell of the sensor assembly of FIG. 9 shown coupling to the inner subassembly of the sensor assembly of FIG. 9, and the deflector assembly of FIG. 9 shown coupled to the inner subassembly of the sensor assembly.
Figure 19:
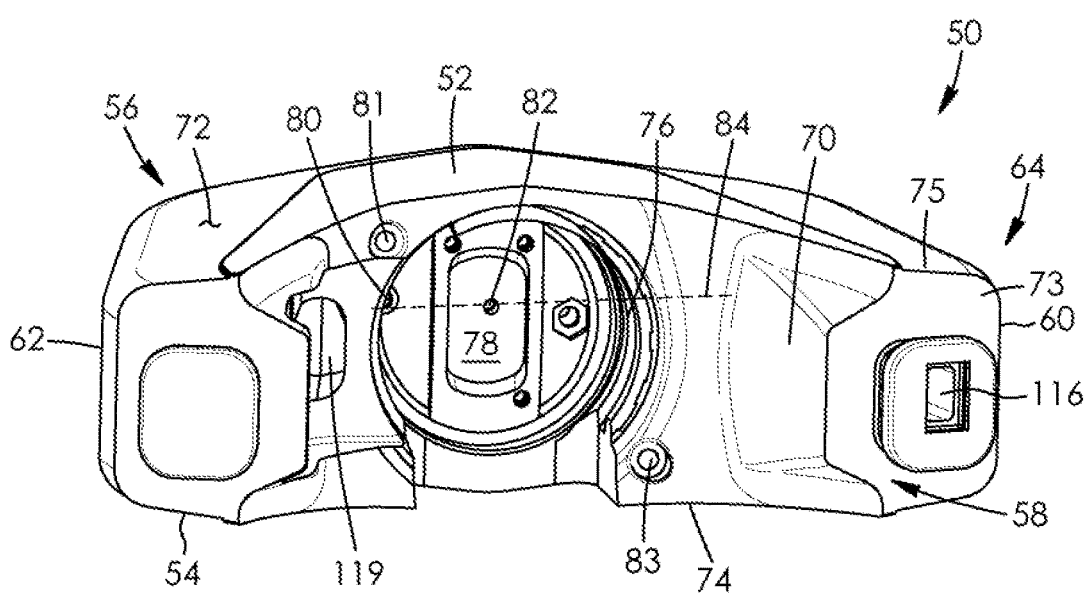
FIG. 19 is a rear, top perspective view of the sensor assembly of FIG. 3, with the deflector assembly not shown.

Referring to FIG. 19, the sensor assembly 64 includes an inner subassembly 70 and an outer shell 72 which extends about the inner subassembly. The inner subassembly is best seen in FIG. 9 and the outer shell is best seen in FIG. 7. Referring to FIG. 10, the inner subassembly 70 includes a female member, in this example a peripheral catch 73 which is c-shaped in profile and which selectively couples with a corresponding male member, in this example peripheral seat 75 of the outer shell.

As seen in FIG. 8, the outer shell 72 further includes one or more protrusions 77 shaped to selectively be received within corresponding recesses 79 of the inner subassembly 70. In this manner, the outer shell 72 selectively couples to the inner subassembly in this example. Referring to FIG. 19, the inner subassembly 70 further includes a pair of fastener apertures 81 and 83 through which fasteners (not shown) extend and engage threaded apertures 85 and 87 of the outer shell 72, seen in FIG. 7, to further secure the sensor assembly 64 together. However these specific mechanisms of snapping and coupling together the outer shell and the inner subassembly are not strictly required and the outer shell and inner subassembly may be coupled together in other manners in other examples.

Referring now to FIG. 19, the inner subassembly 70 includes a threaded portion 76 adjacent to recessed portion 74 of the device 50. The threaded portion extends from the recessed portion towards the front 56 of the device. The inner subassembly 70 includes a disc-shaped planar member, in this example a centrally-positioned outer wall 78 through which extend a plurality of sensor sampling ports, including an oxygen and environmental sensor sampling port 80 and a flow or pressure sampling port, in this example a pressure sensor sampling port 82. The ports approximately align with each other along a horizontal axis 84 in this example when the device 50 is oriented in its upright position and from the perspective of FIG. 19.

Figure 27:
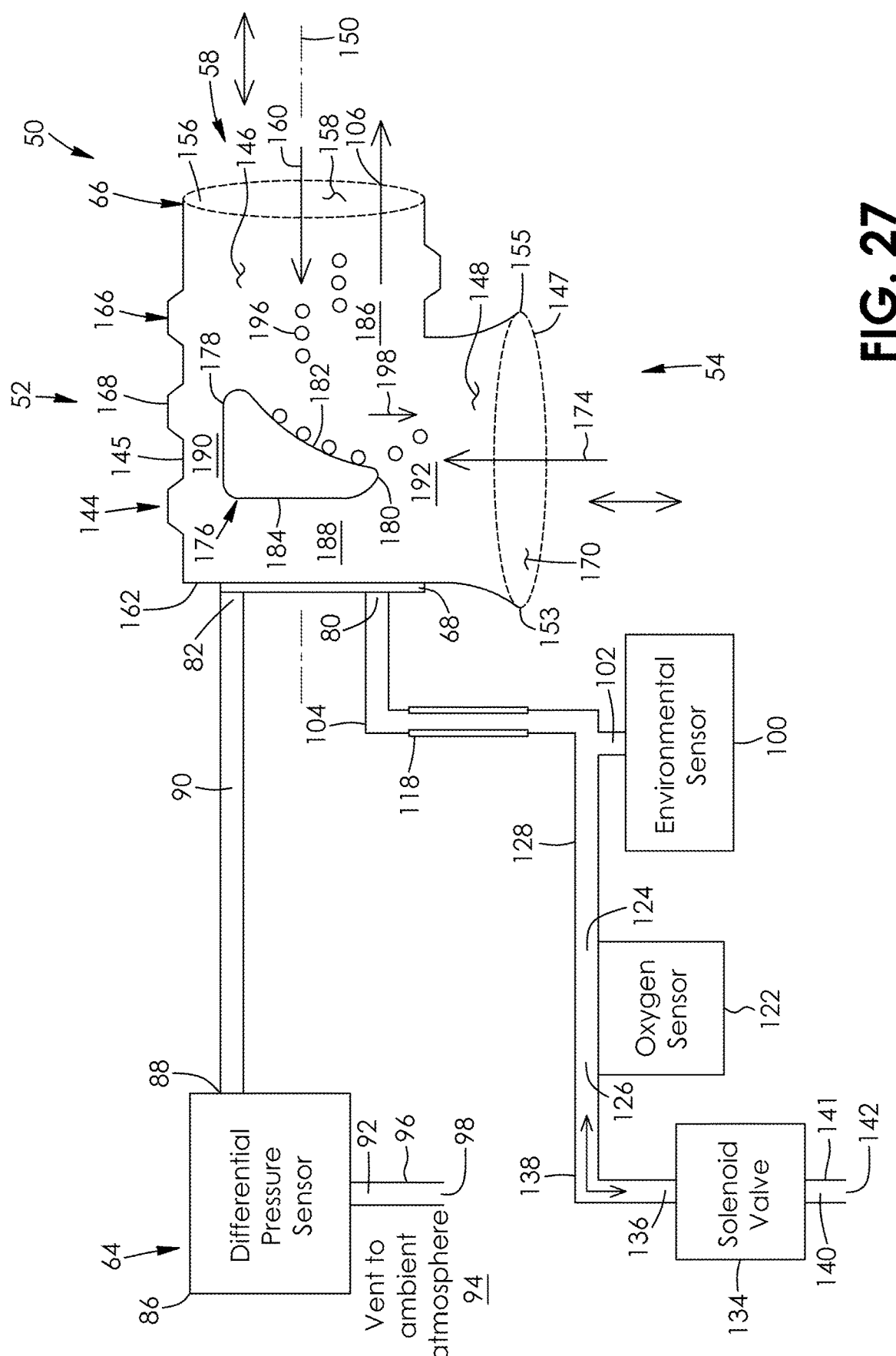
FIG. 27 is a schematic diagram of the ventilation measuring device of FIG. 1.

As seen in FIG. 27, the device 50 includes a flow sensing mechanism or flow sensor, in this example a pressure sensor, in this case a differential pressure sensor 86. The differential pressure sensor in this example is an off-the-shelf product, in this case an AMSS915-type pressure sensor that may be purchased at Analog Microelectronics GmbH, having an address of An der Fahrt 13, 55124 Mainz, Germany. However, this type of sensor is not strictly required and other types of pressure sensors may be used in other embodiments.

The pressure sensor 86 has a first pressure sensor inlet 88 connected to and in fluid communication with pressure sensor sampling port 82 via conduit 90. The pressure sensor has a second pressure sensor inlet 92. The device 50 includes an ambient or open air port 98 and a conduit 96 which extends between the second pressure sensor inlet of the pressure sensor 86 and the open air port. The second pressure sensor inlet 92 of the pressure sensor is thus connected to and in fluid communication with the ambient air/atmosphere 94 via conduit 96 in this embodiment.

Figure 2:
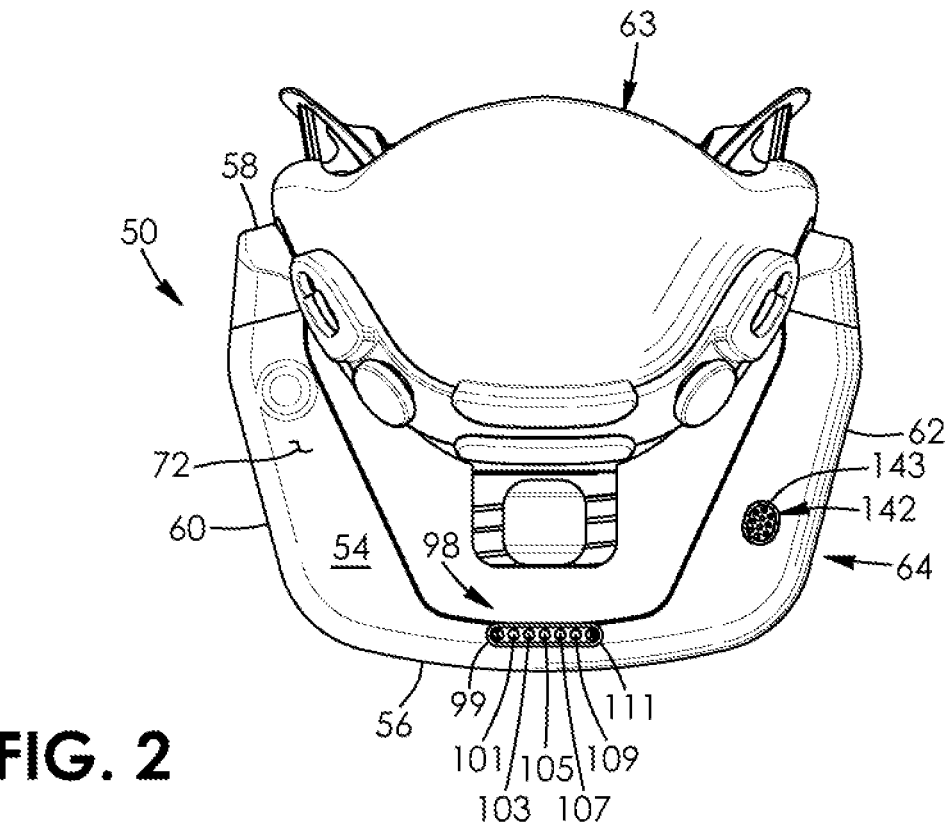
FIG. 2 is a bottom plan view of the measuring device and face mask of FIG. 1.

As seen in FIG. 2, the device 50 includes in this example a plurality of spaced-apart case vents 99, 101, 103, 105, 107, 109 and 111 which are in fluid communication with each other and open air port 98. The vents are positioned between sides 60 and 62 of the device 50 and adjacent to the bottom 54 and front 56 of the device in this example. The vents 99, 101, 103, 105, 107, 109 and 111 extend through outer shell 72 of the sensor assembly 64 in this example.

Referring back to FIG. 27, the device 50 includes an environmental sensor 100. The environmental sensor in this example is an off-the-shelf product, in this case a BME280-type environmental sensor which may be purchased at Bosch Sensortec GmbH, having an address of Gerhard-Kindler-Straße 9, 72770 Reutlingen/Kusterdingen, Germany. However, this type of sensor is not strictly required and other types of environmental sensors may be used in other embodiments. The environmental sensor 100 has a port 102 connected to and in fluid communication with oxygen and environmental sensor sampling port 80 via a passage, in this example conduit 104.

When a person using the device 50 inhales, as seen by arrow of numeral 106 in FIG. 27, the differential pressure sensor 86 is subject to turbulence that is absent in the environmental sensor's pressure output. The device 50 is thus configured to use the change in the environmental sensor's pressure output to determine the inhale flow rate. This circumvents signal noise which may otherwise occur in the differential pressure sensor signal during inhales. The environmental sensor 100 also outputs temperature and relative humidity data for flow calculations and oxygen sensor signal correction. Differential pressure is used to calculate both inhale and exhale flow rates. In another embodiment, absolute pressure inhale flow sensing may optionally be used.

The pressure sensor output is used for breath state detection and exhale flow rate calculations. The pressure sensor 86 is used to detect breath state by means of a zero-crossing check of the differential pressure sensor output with consideration to the sensor's signal noise threshold. If the breath state is in an exhale direction, the differential pressure sensor output is used to compute the instantaneous flow rate between data samples. If the breath state is in an inhale direction, the difference between the environmental sensor pressure output and ambient pressure is used to compute an instantaneous flow rate between data samples. Ambient pressure is considered to be the last environmental sensor pressure output where no breathing has occurred. The instantaneous flow volume between data samples is calculated using each gap's instantaneous flow rate. When the breath state returns to no breathing, all of the instantaneous flow volumes for the completed breath segment are summed. This sum is known by those skilled in the art as tidal volume (Tv(L)). Breath segment frequency is then calculated using the following formula: (segment Rf)= 30 s/(breath segment time(s)). The ventilation (Ve) of the breath segment is calculated using the following formula: Ve(L/min)=(breath segment frequency)×(breath segment tidal volume (L)). For each pair of inhale and exhale segments, average breath segment frequency (Rf), Tv, and Ve are determined as the final flow metrics for the whole breath.

Figure 25:
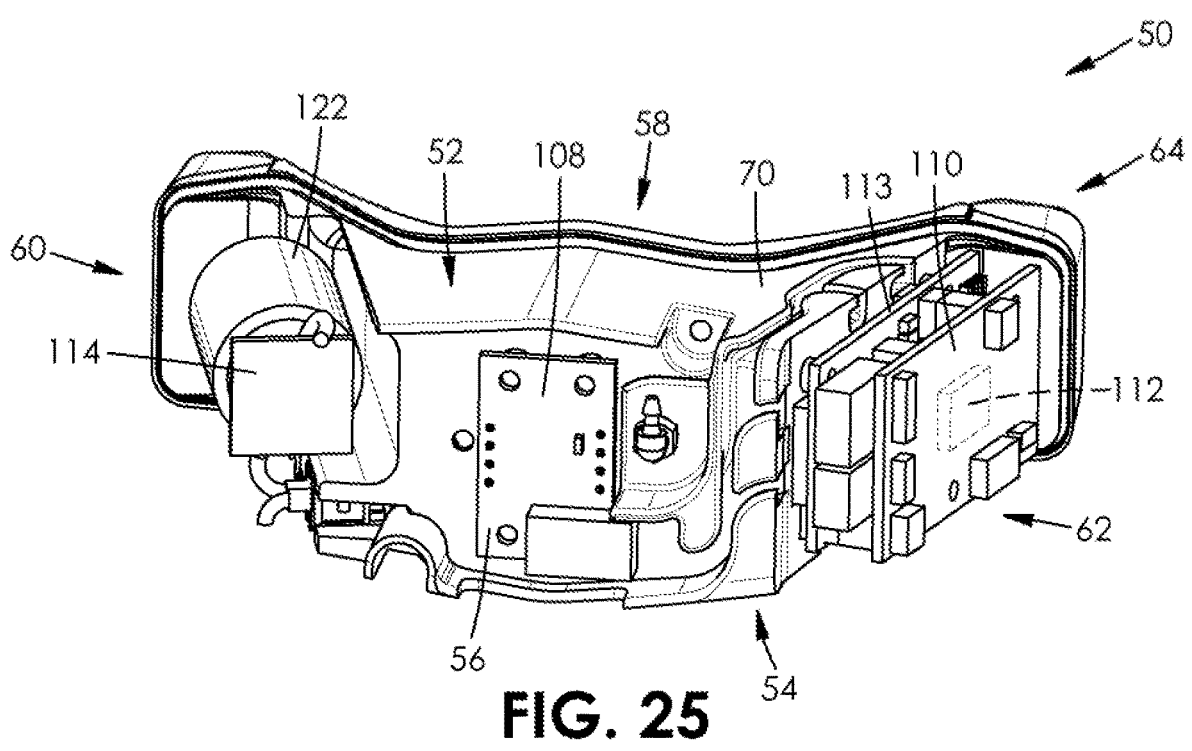
FIG. 25 is a further front perspective view of the inner subassembly of the sensor assembly of FIG. 9.

As seen in FIG. 25, the device 50 includes a circuit board 108 that houses the differential pressure sensor 86 seen in FIG. 27. The device 50 includes circuit boards 110 and 113 which are the main logic and valve control boards. The circuit boards 108, 110 and 113 mount to the inner subassembly 70. The device 50 includes a processor, in this example a microprocessor 112 coupled to circuit board 110. In this case, the microprocessor is an off-the-shelf component of a NRF52832-type which may be purchased at Nordic Semiconductor ASA, having an address of P.O. Box 436, Skoyen, 0213, Oslo, Norway. However, this type of microprocessor is not strictly required and other types of processors may be used in other embodiments. The microprocessor 112 operatively couples with the pressure sensor 86 and environmental sensor 100 seen in FIG. 27, and receives data therefrom. Referring back to FIG. 25, the pressure sensor is on the non-visible side of board 108 and the environmental sensor is on the non-visible side of further environmental sensor circuit board 114 of the device 50.

Figure 20:
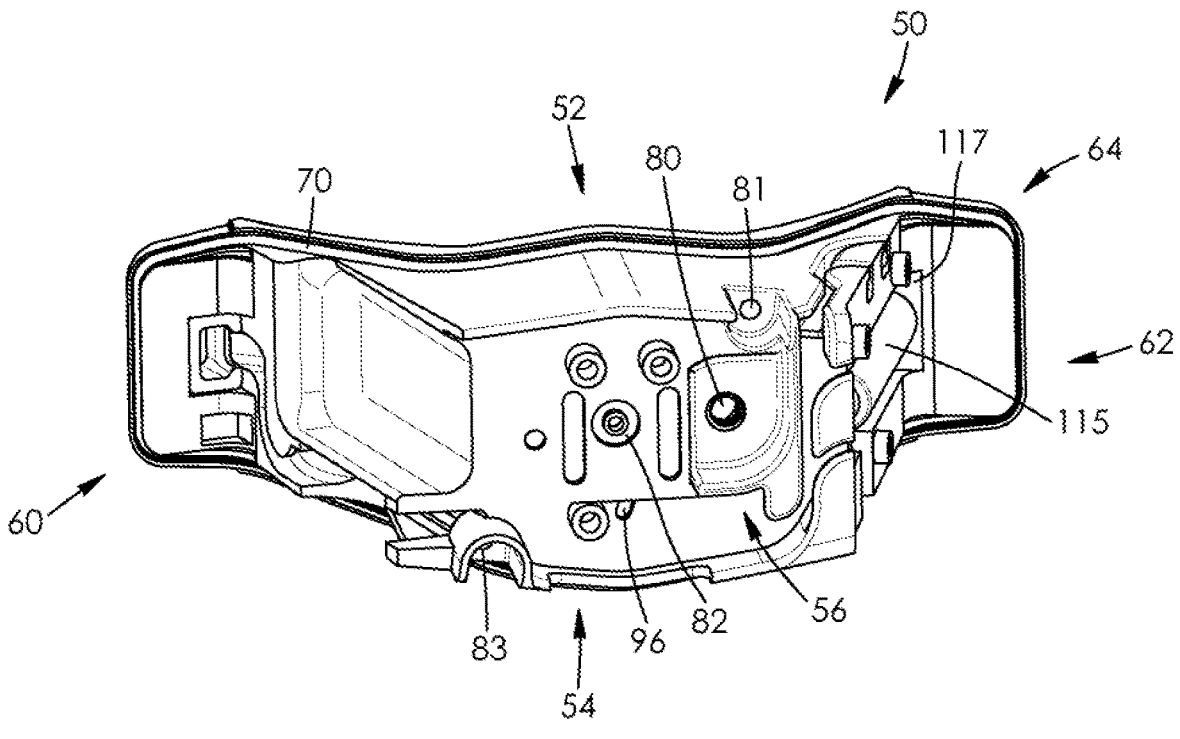
FIG. 20 is a front perspective view of the inner subassembly of the sensor assembly of FIG. 9, with electronic and plastic parts thereof not shown.

As seen in FIG. 20, the device 50 additionally includes a battery 115 for supplying power thereto. The battery is disposed within a recessed battery holder 117 of the inner subassembly 70 located adjacent to side 62 of the device 50. The battery holder is operatively coupled, and in this example soldered to the circuit board 110 seen in FIG. 25. As seen in FIGS. 4 and 19, the device 50 includes a battery door 119 that may be selectively opened to insert and remove the battery as required. The battery door is held in place in this example by the deflector once totally screwed in. In this case, the battery 115 seen in FIG. 20 is a AAA-type battery; however, this type of battery is not strictly required and other types of batteries or power sources may be used in other embodiments. The battery operatively connects to the microprocessor 112 seen in FIG. 25.

As seen in FIG. 19, the device 50 includes an on/off switch, in this example in the form of an on/off plunger switch 116 located adjacent to the rear 58 and side 60 of the device in this example. The plunger switch operatively couples to the circuit boards 110 and 113 seen in FIG. 25. Referring back to FIG. 19, the switch 116 is configured to cut off power to the device upon the switch being pushed inwards towards the circuit board.

As seen in FIG. 27, the device 50 includes a desiccant, in this example the desiccant is a desiccant tube 118 which is part of conduit 104 in this example. The desiccant tube is off-the-shelf components of Nafion™-type tubing, which may be purchased at Perma Pure LLC, having an address of 1001 New Hampshire Ave., Lakewood, New Jersey, 08701, United States of America. The device utilizes passive diffusion of humidity, with the area surrounding the desiccant tube 118 being purged by ambient air.

Still referring to FIG. 27, the device 50 includes an oxygen sensor 122. In this example, the oxygen sensor is a passive sensor and is an off-the-shelf component of the galvanic fuel cell type, which may be purchased at Analytical Industries Inc., having an address of 2855 Metropolitan Place, Pomona, California, 91767, United States of America. However, this type of sensor is not strictly required and other types of oxygen sensors may be used in other embodiments.

Figures 21, 22:
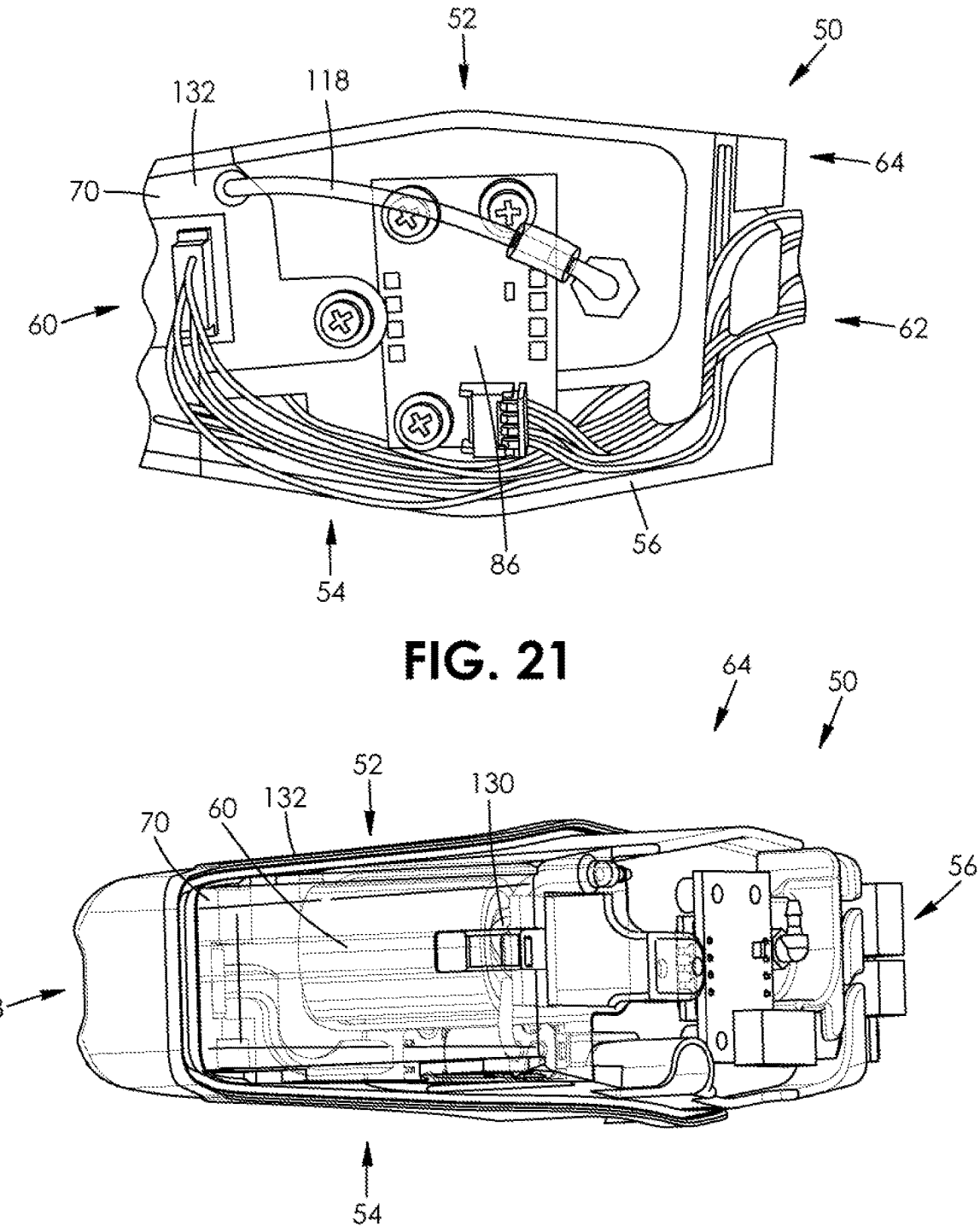
FIG. 21 is a front perspective view of the inner subassembly of the sensor assembly of FIG. 20, with part of an oxygen sensor cartridge, desiccant tubing, a flow sensor and main circuit boards thereof being at least partially shown.
FIG. 22 is a side perspective view thereof, with the oxygen sensor cartridge being shown, the cartridge containing flow channels, and with an environmental sensor, an oxygen sensor, a solenoid valve, a flow sensor and the flow elbow of the inner subassembly also being shown.
Figure 23:
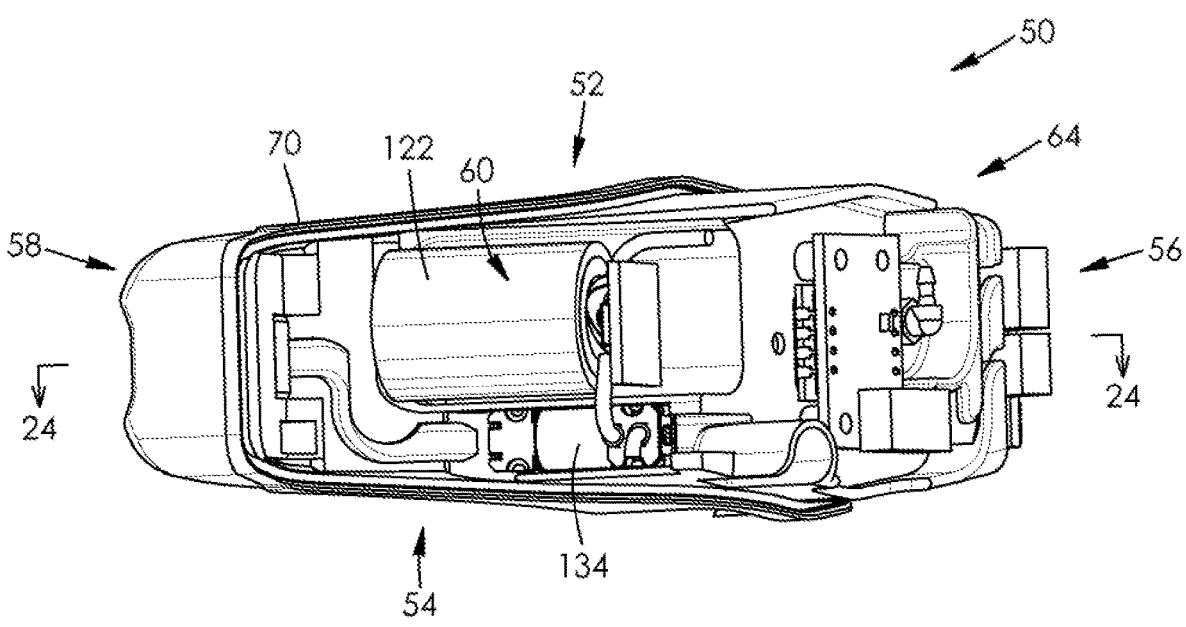
FIG. 23 is a further side perspective view thereof, with internal features of the oxygen sensor cartridge being shown, and the cartridge being shown without its housing that contains the flow channels of FIG. 22.
Figure 24:
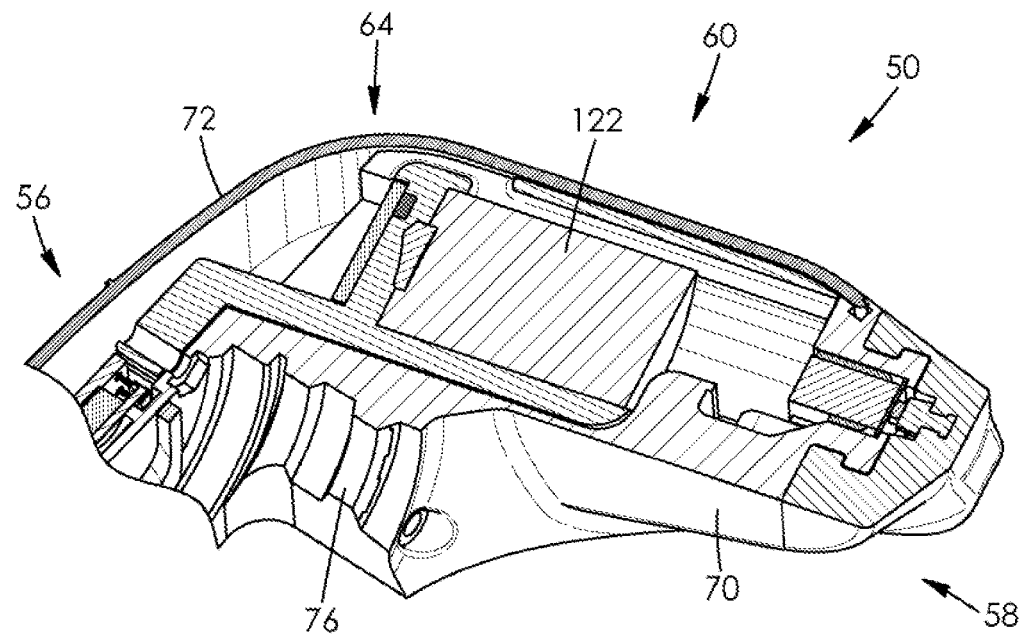
FIG. 24 is a cross-sectional view taken along lines 24-24 of the inner subassembly of FIG. 23, with the oxygen sensor, the environmental sensor, a button circuit board and a flexible button plunger of the inner subassembly being shown.
Figure 26A:
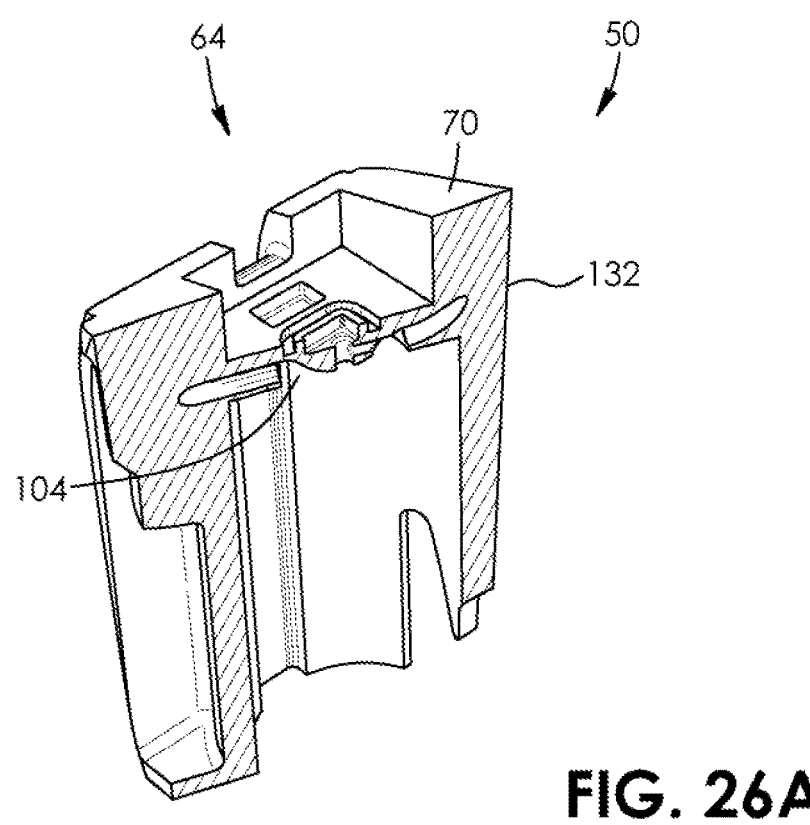
FIG. 26A is a cross-sectional view of an oxygen sensor cartridge mixing chamber, the environmental sensor receptacle and oxygen sensor receptacle of the inner subassembly of FIG. 9.

The oxygen sensor has a pair of oxygen sensor ports 124 and 126 that are in fluid communication with sampling port 80 via conduits 104 and 128. As seen in FIG. 22, the device 50 includes an oxygen sensor micro-mixing chamber 130 that is adjacent to and in communication with oxygen sensor ports 124 and 126 seen in FIG. 27. The oxygen sensor emits an oxygen sensor signal. Referring to FIG. 25, the microprocessor 112 is in communication with and receives data from the oxygen sensor 122 via an analog-to-digital converter (not shown) in this example. As seen in FIG. 26, the device 50 includes an oxygen sensor cartridge or holster 132 in this example shaped to receive the oxygen sensor 122 seen in FIG. 25. The device 50 so shaped and described herein may result in a maximum gas channel flow rate. As a result, by using small desiccant tube 118 seen in FIG. 27, the device 50 as herein described can desiccate sample gas prior to it reaching the oxygen sensor 122.

Figures 26B, 26C, 26D:
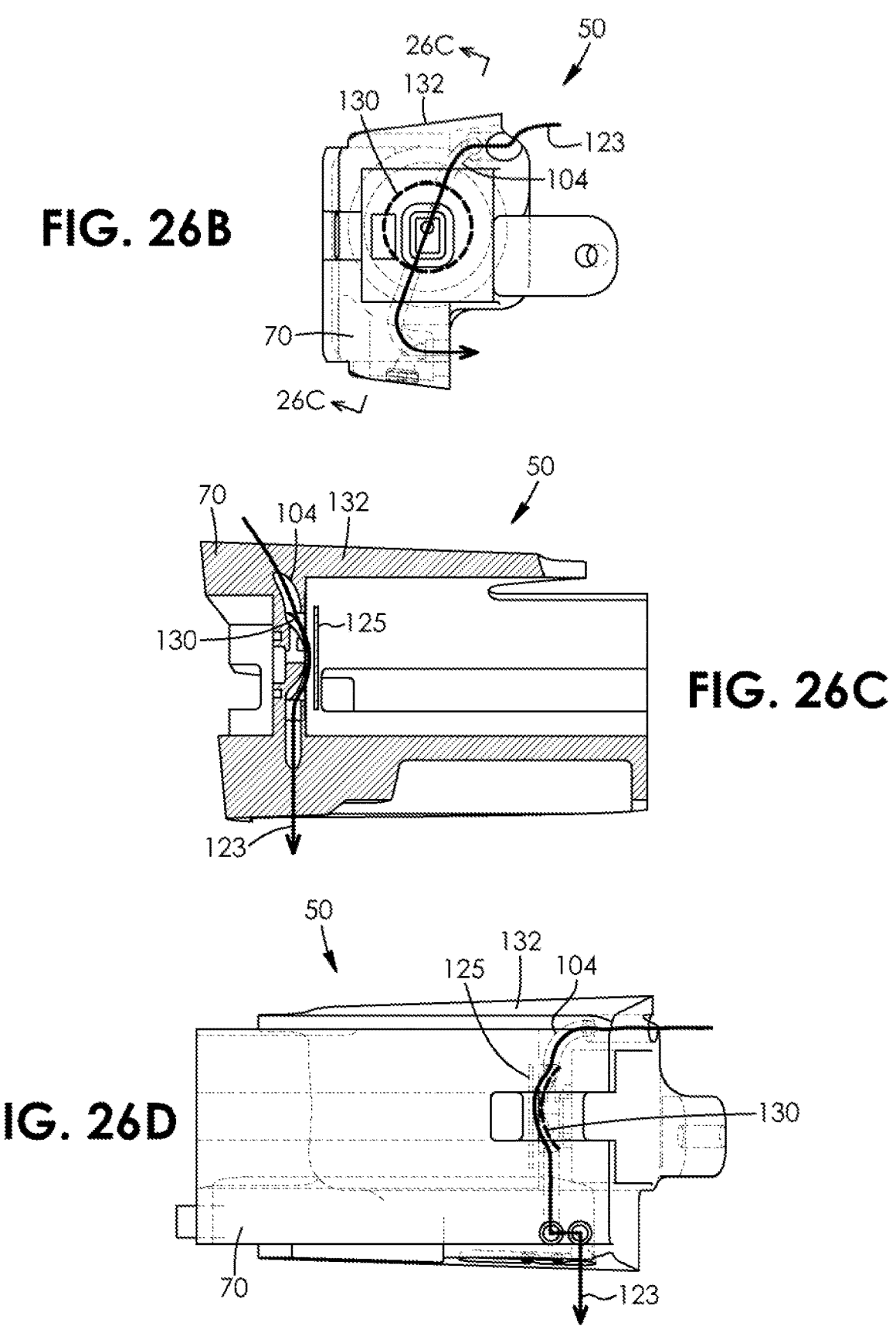
FIG. 26B is a front elevation view thereof, with the oxygen sensor also being shown in ghost.
FIG. 26C is cross-sectional view taken along lines 26C-26C thereof, with the oxygen sensor not being shown.
FIG. 26D is a side elevation view thereof.

Referring to FIGS. 26B to 26D, conduit 104 has a parabolic shape which promotes air flow 123 towards the oxygen cell diffusion membrane 123 seen in FIG. 26C, reducing signal response time thereby. Furthermore, there is a narrow flow channel or conduit 104 from sampling port 80 seen in FIG. 27 into the environmental sensor purge flow channel or conduit 128, which improves gas purging by the environmental sensor 100, resulting in better humidity and temperature readings thereby.

Still referring to FIG. 27, the device 50 includes an electromechanically operated valve, in this example a solenoid valve 134. The solenoid valve is an off-the-shelf component, in this example Parker™ 915-000001-005-type solenoid valve which may be purchased at Parker Hannifin Corp, having an address of 26 Clinton Drive, Hollis, New Hampshire, 03049, United States of America. However, this type of valve is not strictly required and other types of electromechanically operated valve and/or solenoid valves may be used in other embodiments.

A first port 136 of the valve 134 is connected to and is in fluid communication with proximal sampling port 80 in this example via conduits 104, 128 and 138. A second port 140 of the valve 134 is in fluid communication with ambient or open air port 142 via a passageway, in this example conduit 141. As seen in FIG. 2, the device 50 includes a mesh screen 143 which extends across open air port 142. The mesh screen and open air port are positioned adjacent to side 62 of the device 50 and adjacent to the bottom 54 of the device in this example. The above structure is not strictly required and in another embodiment, open air port 142 may be the same as open air port 98 seen in FIG. 2. This is because ports 98 and 142 are similarly situated and thus experience similar air turbulence, and therefore the ambient port of the oxygen sensor may be said to be port 98.

Referring to FIG. 27, the solenoid valve 134 is positioned between oxygen sensor port 126 and ambient port 142 in this embodiment. The valve is thus between and in communication with the oxygen sensor 122 and ambient air 94. The valve 134 is also functionally between and in communication with the environmental sensor 100 and ambient air.

The solenoid valve so positioned and when in a closed position, inhibits ambient air from port 142 passively diffusing into the oxygen sensor 122, whereas the conduits 104, 128 and 138 are sufficiently long that that air from port 80 does not have the time to diffuse to the oxygen sensor during a single breath segment, and therefore will not erroneously bias the settled oxygen sensor reading breath-by-breath in this example.

The valve 134 is configured to be actuated to selectively open. The valve when opened permits fluid communication between the oxygen sensor 122 and the port 142. The valve 134 also enables fluid communication between the environmental sensor 100 and port 142 when the valve is open. The solenoid valve so positioned allows the device 50 to control when the oxygen sensor 122 is purged with new gas. The sampling ports 80 and 82 are configured to expose the sensors 86, 100 and 122 to substantially similar pressure differentials.

Figures 11, 12, 13, 14, 15:
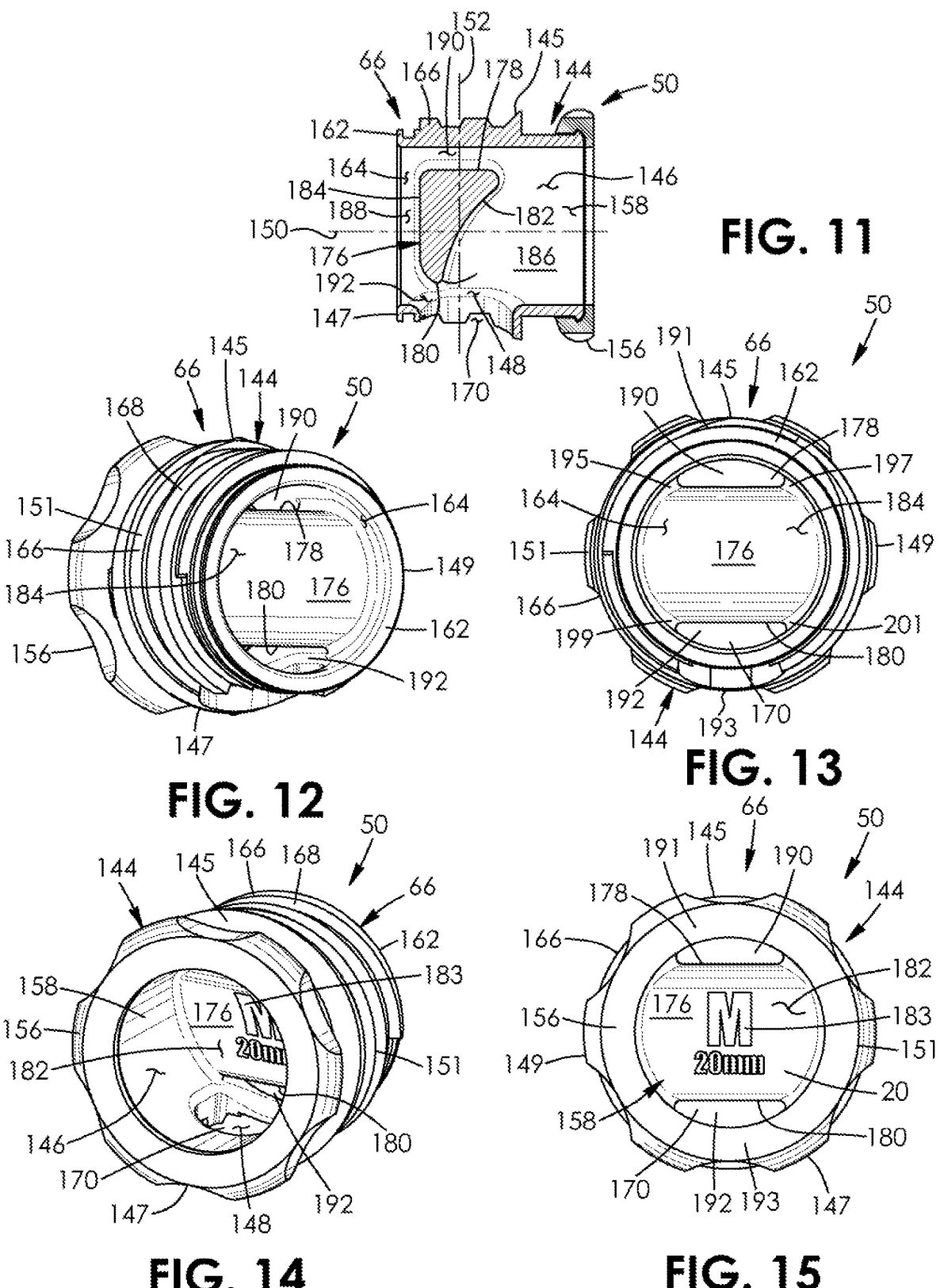
FIG. 11 is a side sectional view taken along line 11-11 of the deflector assembly of FIG. 3.
FIG. 12 is a front, left side perspective view thereof.
FIG. 13 is a rear elevational view thereof.
FIG. 14 is a rear, left side perspective view thereof.
FIG. 15 is a front elevational view thereof.

Referring to FIG. 11, the deflector assembly 66 comprises a conduit 144 that is tubular in this example. As seen in FIG. 14, the conduit has a top 145, a bottom 147, and a pair of spaced-apart sides 149 and 151 in this example which extend between the top and bottom thereof. The conduit 144 includes an exhaled-air receiving portion 146 and an inhaled-air receiving portion 148, which may be referred to as an exhaled-air outlet portion. The exhaled-air receiving portion of the conduit 144 extends along a first longitudinal axis, in this example a horizontal axis 150 when the device 50 is used in its upright and normal operation and from the perspective of FIG. 11. The inhaled-air receiving portion 148 of the conduit extends along a second longitudinal axis, in this example a vertical axis 152 that is perpendicular to the horizontal axis.

The conduit 144 has a proximal or first end, in this example flanged end 156 with a first or proximal opening 158 extending therethrough. The opening is circular in this example. Referring to FIG. 3, flanged end 156 is shaped to selectively couple to mating portions 157 of the face mask adjacent to a central aperture 159 of the face mask 63 in a conventional manner. Referring to FIG. 27, exhalations enter into the proximal opening 158 of the conduit 144 in a first direction, in this example a horizontal direction as shown by arrow of numeral 160 when the device 50 is used in its upright and normal operation and from the perspective of FIG. 27.

Referring back to FIG. 11, the conduit has a second end, in this example flanged end 162, spaced-apart from end 156 thereof. End 162 has a second opening, in this example a circular opening 164 extending therethrough. As seen in FIG. 18, end 162 of the conduit 144 is shaped to receive and abut with filter 68. As seen in FIG. 27, sampling ports 80 and 82 align adjacent with end 162 of the conduit in this example.

Referring to FIG. 11, the conduit 144 includes an enclosing wall 166 that extends between flanged ends 156 and 162 thereof. As seen in FIG. 18, the wall of the conduit includes an outer threaded portion 168 in this example that enables the conduit to selectively threadably couple with threaded portion 76 of inner subassembly 70. Referring to FIG. 11, the conduit 144 has a third, lower or distal opening 170 that extends through wall 166 at the bottom 147 thereof in this example. As seen in FIG. 16, the opening has a constriction width $C_W$ extending between sides 149 and 151 of the conduit 144. The constriction width extends in a direction perpendicular to horizontal axis 150 of the conduit. The opening 170 has a constriction length $C_L$ extending between ends 156 and 162 of the conduit 144. The width and length of the opening are approximately equal in size in this embodiment. As seen in FIG. 27, air to be inhaled enters into the opening 170 of the conduit 144 in a second direction, in this example a vertical direction as shown by arrow numeral 174, which is perpendicular to the exhaling, horizontal axis 150.

Still referring to FIG. 27, the conduit includes one or more outwardly tapered, outwardly flared peripheral portions 153 and 155 adjacent to bottom 147 thereof. As seen in FIG. 16, the tapered peripheral portions extend along opening 170 of the conduit 144 spaced inwardly from sides 149 and 151 of the conduit, respectively.

Referring to FIG. 11, the exhaled-air receiving portion 146 of the conduit extends from the proximal opening 158 towards the opening 170 of the conduit. The inhaled-air receiving portion 148 of the conduit 144 extends from opening 170 towards the proximal opening of the conduit. As best seen in FIG. 14, the proximal opening 158 of the conduit 144 has a cross-sectional area that is larger than that of the opening 170 of the conduit in this example.

Referring to FIG. 11, the deflector assembly 66 includes a divider or deflector 176 disposed within the conduit 144. The deflector is generally in the shape of a triangular prism in this example; however, this is not strictly required and the deflector may comprise other shapes in other embodiments. As seen in FIG. 12, the deflector 176 extends between opposite sides 149 and 151 of the deflector assembly 66.

As seen in FIG. 11, the deflector has a first or upper peripheral portion 178 that is generally planar and which extends parallel to horizontal axis 150 of the conduit 144 in this example. The upper peripheral portion of the deflector 176 is positioned near the top 145 of the conduit 144 in this example. The deflector has a second or lower peripheral portion 180 that is arcuate-shaped and convexly curved in side profile in this example. The lower peripheral portion of the deflector 176 is positioned near the bottom 147 of the conduit in this example. As seen in FIG. 12, the peripheral portions 178 and 180 of the deflector extend between the sides 149 and 151 of the deflector assembly 66. Referring to FIG. 11, the upper peripheral portion of the deflector 176 is thicker than the lower peripheral portion 180 of the deflector in this embodiment. The deflector tapers from the upper peripheral portion 178 thereof to the lower peripheral portion 180 thereof in this example.

As seen in FIG. 11, the deflector has a first or rearward surface 182 that is concave in this example and which faces proximal opening 158 of the conduit 144. As seen in FIG. 14, the deflector includes indicia 183 on the rearward surface thereof which in this example includes a capital letter M, together with the wording "20 mm V0.18.14". This means that the constriction width $C_W$ is equal to 20 mm in this example.

Referring to FIG. 11, the deflector 176 has a second or forward surface 184 opposite to the rearward surface thereof. The forward surface of the deflector is planar, extends parallel to vertical axis 152 of the conduit 144 and faces opening 164 of the conduit in this example. The surfaces 182 and 184 of the deflector 176 extend between the peripheral portions 178 and 180 of the deflector.

As seen in FIG. 27, the deflector partially defines a primary channel or chamber 186 through which air primarily flows between openings 158 and 170 of the conduit 144. Rearward surface 182 of the deflector 176 faces and is in fluid communication with the primary chamber. The deflector 176 is shaped to direct air passing therethrough primarily through the primary chamber 186 of the device 50.

The deflector also partially defines a second channel or secondary chamber 188 through which a reduced amount of the air flows between the openings 158 and 170 of the conduit 144. The secondary chamber is smaller in volume compared to the primary chamber 186 and is cylindrical in shape in this example. Forward surface 184 of the deflector 176 faces and is in fluid communication with the secondary chamber 188. Sampling ports 80 and 82 are positioned within the secondary chamber and are forward of the deflector in this example. Sensors 86, 100 and 122 are thus in fluid communication with the secondary chamber 188 of the conduit 144. The deflector 176 is shaped to inhibit external liquid, such saliva 196, from coming into contact with the sampling ports.

The secondary chamber 188 is in fluid communication with the primary chamber 186 via a first passageway 190. The first passageway extends adjacent to the top 145 of the conduit 144 in this example, is aligned with the exhaled-air receiving portion 146 of the conduit 144 and is in fluid communication with the proximal opening 158 of the conduit. As seen in FIG. 11, the first passageway is rectangular in shape when viewed in side section in this example. As seen in FIGS. 13 and 15, the passageway 190 is a circular segment when viewed in rear and front elevations in this example. Referring to FIG. 13, the first passageway 190 is enclosed by upper peripheral portion 178 of the deflector 176, an arc-shaped portion 191 of wall 166 thereabove adjacent to the top 145 of the conduit 144, and a pair of spaced-apart webs 195 and 197 extending between the upper peripheral portion of the deflector and the arc-shaped portion of the wall in this example. The first passageway is positioned above the deflector 176 in this example and may be regarded as an upper opening of the deflector.

Referring back to FIG. 27, the deflector assembly 66 includes a second passageway 192 aligned with the inhaled-air receiving portion 148 of the conduit 144. The second passageway is adjacent to and in fluid communication with opening 170 of the conduit in this example. The second passageway 192 is positioned below the deflector 176 in this example and may be regarded as a lower opening of the deflector. The primary chamber 186 and secondary chamber 188 are in fluid communication with each other via the passageways 190 and 192. As seen in FIGS. 13 and 15, the second passageway 192 is a circular segment when viewed in rear and front elevation in this example. Referring to FIG. 13, the second passageway 192 is enclosed by lower peripheral portion 180 of the deflector 176, an arc-shaped portion 193 of wall 166 therebelow adjacent to the bottom 147 of the conduit 144, and a pair of spaced-apart webs 199 and 201 extending between the lower peripheral portion of the deflector and the arc-shaped portion of the wall in this example.

As seen in FIG. 27, the deflector 176 is configured to direct exhaled-air, as shown by arrow of numeral 160, from the proximal opening 158 to the opening 170 of the conduit 144. The deflector is thus shaped to deflect air exhaled into the exhaled-air receiving portion of the conduit away from sensors 86, 100 and 122. The deflector 176 is configured to cause the sensors to be subject only to a portion of the air exhaled into the exhaled-air receiving portion 146 of the conduit 144: that portion of the air which flows over the top of upper peripheral portion 178 of the deflector, past passageway 190 and into the secondary chamber 188.

Referring to FIG. 27, the oxygen sensor 122 is supplied with exhaled air by means of a positive differential pressure referenced between the proximal end 156 of the conduit 144 and ambient air. The oxygen sensor is also supplied with ambient air by means of a negative differential pressure referenced between the proximal end 156 of the conduit 144 and ambient.

The deflector is also configured to direct inhaled-air, as shown by arrow of numeral 174, from opening 170 to the proximal opening 158 of the conduit. The rearward surface 182 of the deflector 176 is shaped and angled to deflect saliva 196 passing through the exhaled-air receiving portion 146 of the conduit 144 downwards, through the inhaled-air receiving portion 148 of the conduit and outwards from the device 50, as shown by arrow of numeral 198.

Figure 31:
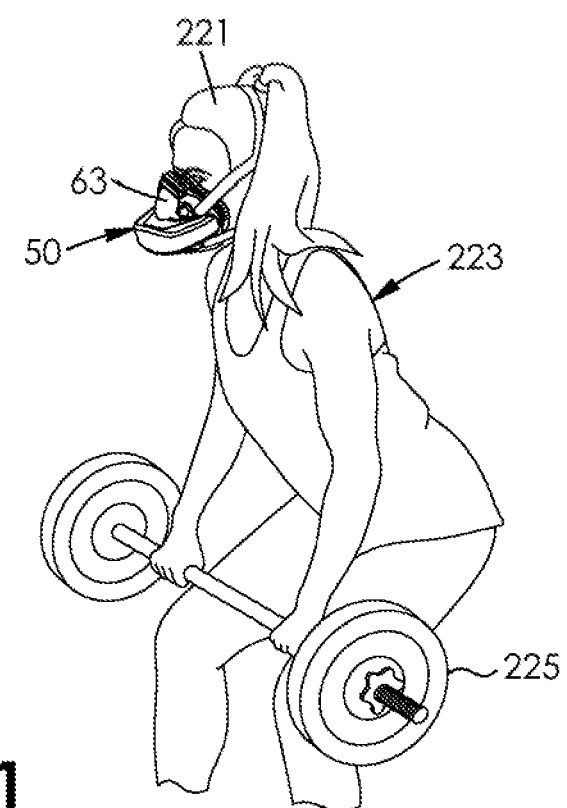
FIG. 31 is a perspective, fragmentary view of the face mask and ventilation measuring device of FIG. 1 shown in use and worn by a person who is lifting weights.
Figure 32:
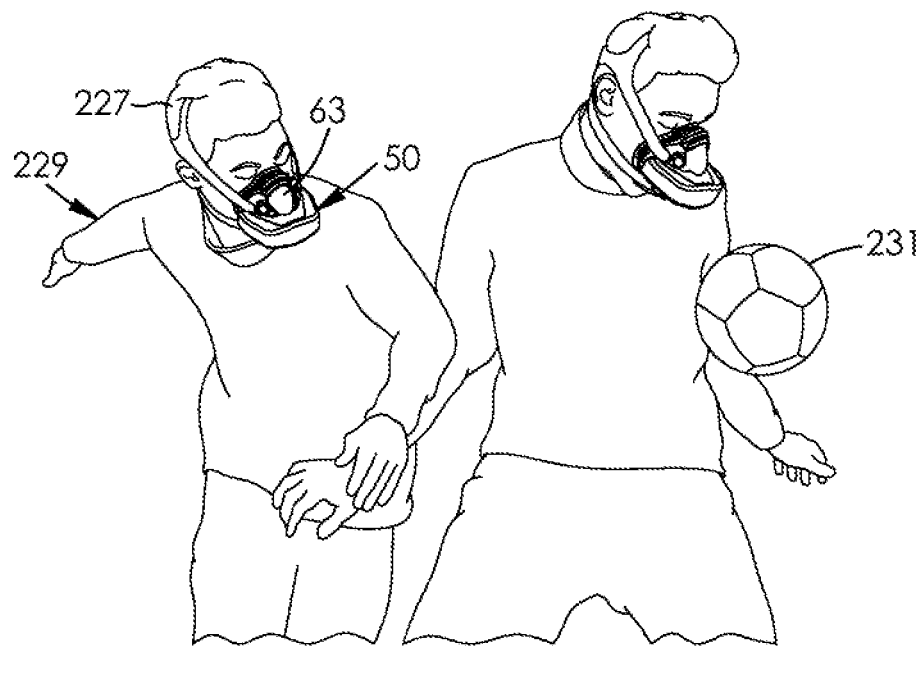
FIG. 32 is a perspective, fragmentary view of face masks and ventilation measuring devices of the type shown in FIG. 1 in use and worn by persons who are playing soccer.

FIGS. 28 to 32 show the device 50 in use for a variety of exemplary exercises. In particular, FIG. 28 shows the mask 63 extending about the head 203 of a person 205 who is running around a track 207, with the device 50 coupled to the mask. FIG. 29 shows the device and mask extending about the head 209 of a person 211 who is exercising using an elliptical machine 213. FIG. 30 shows the device 50 and mask 63 extending about the head 215 of a person 217 who is biking on a road bike 219. FIG. 31 shows the device and mask extending about the head 221 of a person 223 who is lifting weights 225. FIG. 32 shows a pair of devices 50 and masks 63 extending about the heads of persons, such as head 227 of person 229, who are playing soccer with a soccer ball 231.

Figures 33A, 33B:
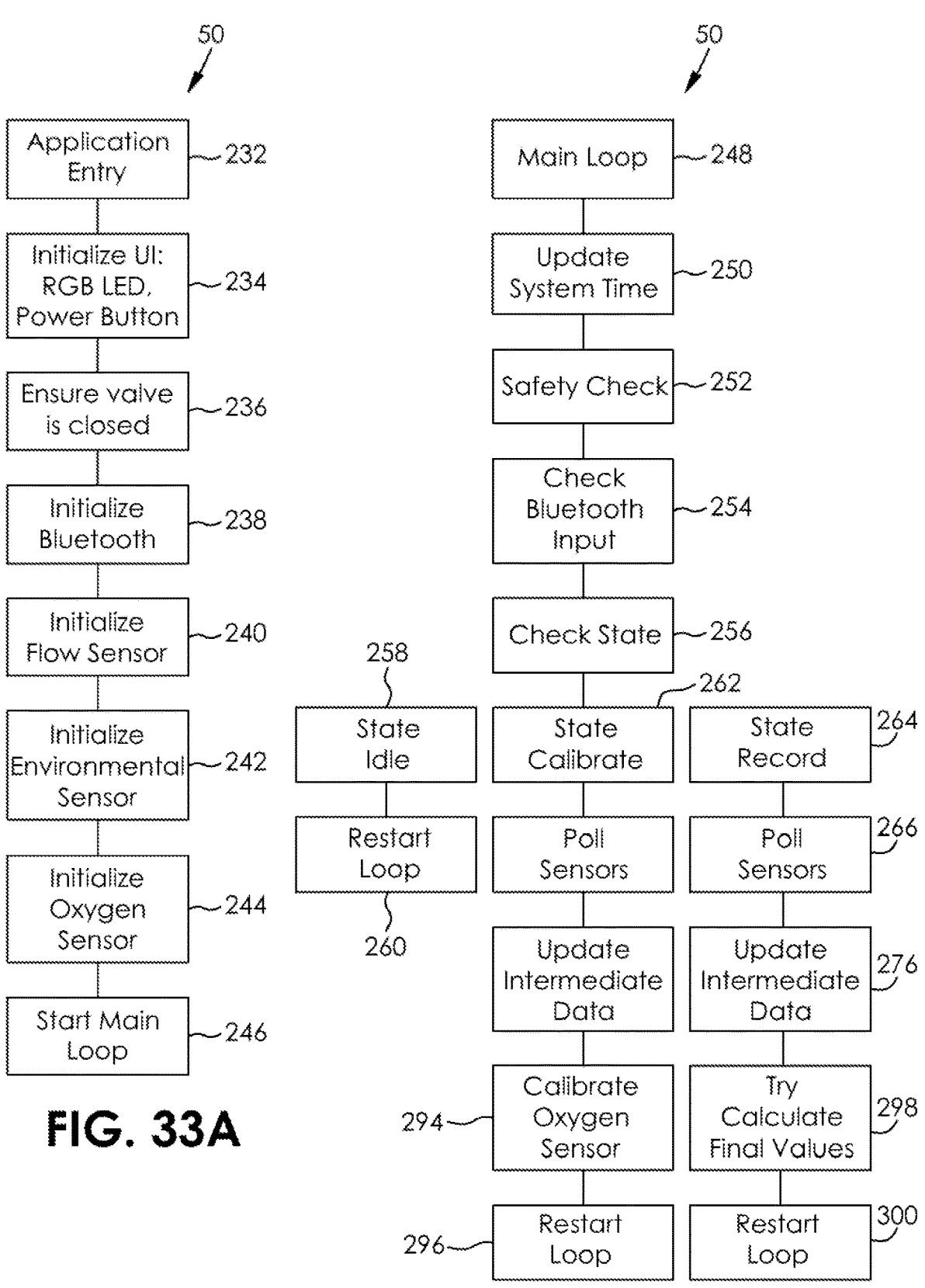
FIGS. 33A to 33E are flow charts showing the operation of the ventilation measuring device of FIG. 1.

FIGS. 33A to 33E are flow charts of showing the operation of the ventilation measuring device of FIG. 1. The following is a description of the same.
Application Entry:

Referring to FIG. 33A, the starting point of the device's logic upon start-up for application entry 232 is as follows. As shown by box of numeral 234, initialize user interface ("UI"): red, green and blue ("RGB") LED and Power Button. This includes configuring the LED digital pins and configuring the power button digital interrupt. The LED is used to display a device heartbeat in RED, inhale breath state in GREEN, and exhale breath state in BLUE.

Next, the device 50 ensures that the solenoid valve 134 seen in FIG. 27 is closed. This step is shown in FIG. 33A by box of numeral 236. This includes making sure that the valve is in its closed state upon start-up since Update Valve State assumes this is the default state.

Still referring to FIG. 33A, the device 50 next initializes wireless communication technology, in this example Bluetooth™, as shown by box of numeral 238. This includes enabling the on-board Bluetooth™ transceiver and beginning Bluetooth™ low energy ("BLE") advertising in order to connect to a Bluetooth™-enabled host device.

The device 50 next initializes the flow sensor, in this case differential pressure sensor 86 seen in FIG. 27. This step is shown in FIG. 33A by box of numeral 240. This step includes sending by the means of two wire interface ("TWI") communication the initialization commands of the sensor as specified by the flow sensor manufacturer.

The device 50 next initializes the environmental sensor 100 seen in FIG. 27. This step is shown in FIG. 33A by box of numeral 242. This step includes sending by the means of TWI communication the initialization commands of the environmental sensor as specified by the environmental sensor manufacturer.

The device 50 next initializes the oxygen sensor 122 seen in FIG. 27. This step is shown in FIG. 33A by box of numeral 244. This step includes sending by the means of TWI communication the initialization commands of the analog-to-digital converter ("ADC") that reads the oxygen sensor analog signal, as specified by the ADC manufacturer.

The device 50 next proceeds to Start Main Loop, as shown by box of numeral 246. The device thus proceeds to the start of its "Main Loop" as shown by box of numeral 248 and FIG. 33B.
Main Loop This infinite loop runs approximately every 20 milliseconds ("ms") until the device 50 is either shut off or runs out of battery charge.

Referring to FIG. 33B, the main loop includes updating system time, as shown by box of numeral 250. This step involves updating the time since the device 50 was turned on, and is to be used globally in all time-based calculations.

Figures 33C, 33D, 33E:
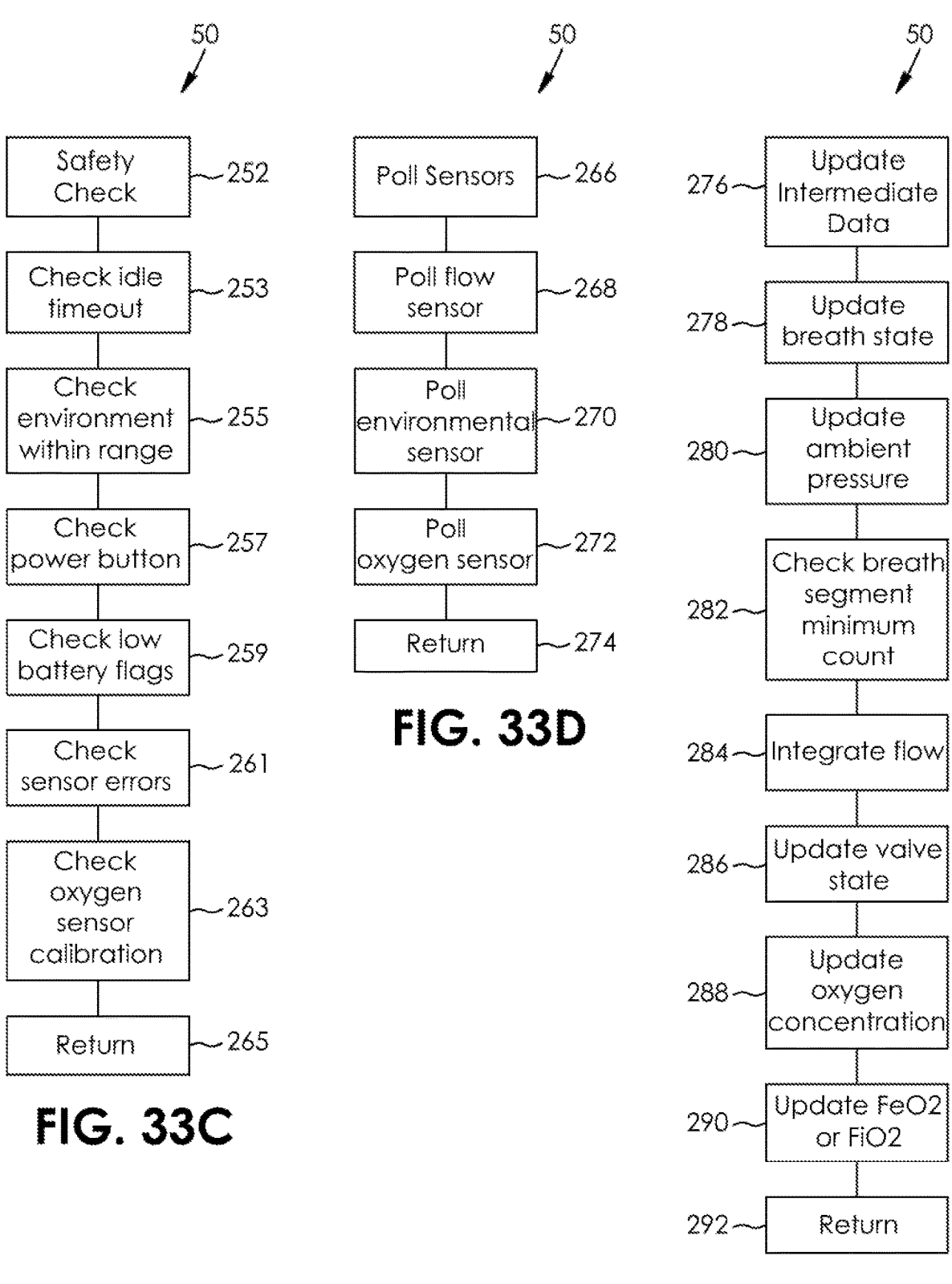

The main loop includes a safety check, as shown by box of numeral 252. The safety check involves checking for conditions that may cause the device 50 to turn off or to recalibrate its sensors 86, 100 and 122 seen in FIG. 27. As seen in FIG. 33C, the safety check includes checking for any idle timeouts 253. This step involving checking if no breathing has occurred for 3 minutes, for example. If so, the device 50 is configured to shut off due to inactivity.

The safety check 252 includes checking that the environment is within range 255. This involves ensuring that the device 50 is not over-heating or under-heating, and that oxygen sensor humidity is not at a level that could cause damage. If temperature is out of range, the device 50 warns the user by means of wireless transmission to a software application, or app, followed by an on-screen message, and shuts itself off. If humidity is out of range, the device 50 is configured to switch into an inhale-only $O_2$ purge using the valve 134 seen in FIG. 27, to purge conduits 104, 128, 138 or oxygen sensor gas line with only ambient air, until humidity reaches a safe level.

Referring back to FIG. 33C, the safety check 252 includes checking functioning of the power button 257. This involves determining if the device 50 should be turned off based on user input.

The safety check includes checking for any low battery flags 259. This involves determining if the device 50 should be shut off based on the current battery level, to avoid brown-out and erroneous measurements. The device 50 is configured to send low battery and dead battery warnings to the host Bluetooth™ device when appropriate.

The safety check 252 includes checking for any sensor errors 261. This involves checking if anything went wrong in communicating with the peripheral sensors. If an error occurs, the device 50 is configured to attempt to transmit it to the Bluetooth™ host controller and await shut-off. Normal operation cannot continue if a fatal sensor error is received.

The safety check 252 includes checking for oxygen sensor calibration 263 and thereafter returning 265 to the main loop 248 seen in FIG. 33B. The checking for oxygen sensor calibration feature will be discussed in greater detail below.

As seen in FIG. 33B, the main loop includes checking Bluetooth™ Input, as shown by box of numeral 254. This involves checking if there are any incoming Bluetooth™ commands from any connected host device. The device 50 sends and receives information with the host related to the deflector assembly 66 {user piece size: SMALL, MEDIUM, LARGE}, volume correction mode {Standard Temperature and Pressure Dry ("STPD"), Body Temperature, Pressure, Saturated ("BTPS")}, state {IDLE, CALIBRATE, RECORD}, oxygen sensor calibration information, errors and warnings generated, and oxygen sensor age.

The main loop includes Checking State, as shown by box of numeral 256. This involves determining what logic to perform based on the current state of the device 50.

a. State Idle, box of numeral 258: in this state the device 50 is awaiting for input from a host Bluetooth™ device in order to begin calibrating and recording. The loop is thereafter restarted, as shown by box of numeral 260.

b. State Calibrate, box of numeral 262: In this state the device is calibrating its oxygen sensor 122 seen in FIG. 27 to ambient measurements.

c. State Record, box of numeral 264: in this state the device 50 is recording ventilatory and metabolic data from a user's breath and transmitting said information to any connected host Bluetooth™ device.

Both the State Calibrate 262 and State Record 264 states involve the step of polling sensors 86, 100 and 122 seen in FIG. 27. This step is shown in FIG. 33D by box of numeral 266 and involves requesting the latest instantaneous values from the flow, environmental, and oxygen sensors by the means of TWI communication.

The polling of the sensors includes retrieving the latest values from the flow sensor, in this case differential pressure sensor 86 seen in FIG. 27. This step is shown in FIG. 33D by box of numeral 268. This involves requesting the latest differential pressure value from the pressure sensor.

The polling of the sensors 266 includes retrieving the latest values from the environmental sensor 100 seen in FIG. 27. This step is shown in FIG. 33D by box of numeral 270. This involves requesting the latest absolute pressure, temperature, and relative humidity values from the environmental sensor situated in the mixing chamber 130, seen in FIG. 22, of the oxygen sensor.

The polling of the sensors 266 includes retrieving the latest values from the oxygen sensor 100 seen in FIG. 27. This step is shown in FIG. 33D by box of numeral 272. This involves requesting the latest oxygen sensor voltage reading. The voltage of the cell is linearly proportional to the partial pressure of oxygen present. The device 50 thereafter returns, as shown by box 274, to the step of updating intermediate data, as shown by box of numeral 276 in FIGS. 33B and 33E.

As seen in FIG. 33E, the updating intermediate data involves ventilatory and metabolic intermediate values related to recent sensor data collected. In particular, this involves updating values that result from computations of the sensor data, and that are used in calculating the final ventilatory and metabolic values reported to the user by the means of the Bluetooth™-enabled host.

Referring to FIG. 33E, the update intermediate data 276 includes updating the breathe state data 278. This involves determining in which direction the user is breathing based on the differential pressure signal of the pressure sensor 86 seen in FIG. 27. If the signal is positive, exhale is occurring, and if the signal is negative, inhale is occurring. If the signal remains about zero, then no breathing is occurring. Breath state possible values are: {NONE, EXHALE, INHALE}.

Referring back to FIG. 33E, the update intermediate data 276 includes updating ambient pressure data 280. Ambient pressure is assigned the value of the absolute pressure of the environmental sensor 100 seen in FIG. 27 only if the differential pressure value of the pressure sensor 86 is approximately zero. When the differential pressure is not nearly zero, breathing is occurring, which causes either a positive or negative hysteresis in the environmental sensor's absolute pressure measurement.

Referring back to FIG. 33E, the update intermediate data 276 includes checking the breath segment minimum count 282. A software-driven de-bounce is applied to reject high frequency noise in breath state. A breath state is only considered valid once it has persisted for at least five Main Loops 248 seen in FIG. 33B in this example, with each main loop having a period of approximately 20 milliseconds in this example. At the beginning of valid breath state EXHALE, the inhale intermediate flow data is reset. At the beginning of valid breath state INHALE, the exhale intermediate flow data is reset. Once valid breath state of NONE has persisted for 1 second, all intermediate flow and oxygen-related data is reset.

As seen in FIG. 33E, the update intermediate data 276 includes integrating flow 284. This involves calculating the Tidal Volume of a breath segment by integrating the instantaneous flow rates between samples. This is done by firstly determining the flow rate since the last loop using the standard Venturi formula $$Q = A_2 \sqrt{\frac{2(p_1 - p_2)}{\rho\left(1 - \left(\frac{A_3}{A_1}\right)^2\right)}}$$

Where Q is the flow rate, A1 and A2 are cross-sectional areas of the venturi proximal and distal ends, (p1–p2) is differential pressure across the venturi, and ρ is humid density. Secondly, the volume passed thru the venturi since the last Main Loop 248 seen in FIG. 33B is determined by multiplying the flow rate by the time elapsed. Thirdly, the volume passed through the venturi between each sample is summed for the whole breath segment, producing a measurement of Tidal Volume for both INHALE and EXHALE breath state. The venturi in this case refers to conduit 144 seen in FIG. 11.

As seen in FIG. 33E, the update intermediate data 276 includes updating the valve state data 286. The valve 134 seen in FIG. 27 is operated to be either open only on breath state inhale, or open only on breath state exhale. Inhale-only purging allows the device 50 to purge the oxygen sensor 122 with ambient air, while exhale-only purging allows the device to purge the oxygen sensor with exhaled air. Possible valve purge modes include: {PURGE_INHALE, PURGE_EXHALE}. If the device state is:

Calibrate: PURGE_INHALE

Record: PURGE_EXHALE

As seen in FIG. 33E, the update intermediate data 276 includes updating oxygen concentration data 288. The oxygen sensor ADC signal is converted to oxygen concentration by this formula: o2Percent=adcReading*o2Coef. o2Coef is defined in the oxygen sensor calibration method. o2Percent is then linearly compensated for any drift in humid density. An average of o2Percent is taken for each breath segment and stored as o2InhaleAvg and o2ExhaeAvg.

As seen in FIG. 33E, the update intermediate data 276 includes updating Fraction of Expired Oxygen ("FeO2") or Fraction of Inspired Oxygen ("FiO2") data 290. If a breath segment has just finished, evidenced by a change in breath state, the device 50 stores the average oxygen concentration for that segment as either Fraction of Expired Oxygen (FeO2) or Fraction of Inspired Oxygen (FiO2). The device 50 thereafter returns, as shown by box 292, to the main loop 248 shown in FIG. 33B.

As seen in FIG. 33B, within the State Calibrate 262 mode, the device 50 next calibrates the oxygen sensor 122 seen in FIG. 27. Referring back to FIG. 33B, this step is shown by box of numeral 294. This involves calibrating the oxygen sensor by purging the oxygen sensor gas line with ambient air by the means of PURGE_INHALE valve operation. Let the oxygen and environmental sensor signals settle for approximately 15 seconds with ambient air input. Once the signals have settled, their measurements are stored. The ambient ADC reading of the oxygen sensor signal is assumed to be a measurement of concentration 20.946% $O_2$. Using this ADC measurement, and a static zero crossing of 0V, a linear transformation between any ADC reading and oxygen concentration is realized; o2Coef=(20.946%–0%)/(ambientAde–0).

Using this coefficient, any measurement of the $O_2$ sensor ADC signal can be converted: o2Percent=adcReading*o2Coef.

Furthermore, since the oxygen sensor measures the partial pressure of oxygen, linear compensation must be applied for any drift in humid density. Humid density may be calculated using standard approximation algorithms. Drift in humid density is a drift in any of absolute pressure, temperature, or relative humidity, from the ambient values recorded at the time of calibration. Once the device 50 has calibrated the oxygen sensor 122 seen in FIG. 27, the main loop is restarted. This is shown by box of numeral 296 in FIG. 33B.

The device 50 next enters within the State Record 264 mode. After updating intermediate data 276, the device 50 tries to calculate final values, as shown by box of numeral 298. Using the intermediate ventilatory, oxygen concentration, and environmental parameters, the device 50 calculates the final breath values and reports them to the host Bluetooth™ device.

Final values are only calculated if the end of a breath is detected, measured by the current breath state being inhale and the last breath state not being inhale, and only if the breath is not too short, does not contain too many changes in breath state, or is not too small in volume as determined by pre-set threshold criteria.

Calculations:

1. Calculate Breathing Frequency: 60 s/breathPeriod[s]
2. Calculate Tidal Volume ("BTPS") as the average between the intermediate data inhale and exhale tidal volumes.

3. Calculate Ventilation: Tidal Volume ("BTPS")*Breathing Frequency.
4. Calculate VO2
   a. Convert Tidal Volume ("BTPS") to Tidal Volume ("STPD").
   b. Calculate Ventilation ("STPD") using Tidal Volume ("STPD").
   c. Calculate VO2 ("STPD"): VO2 ("STPD")=Ventilation ("STPD")*(20.946–FeO2). Those skilled in the art will understand the volume standards BTPS and STPD, how to convert between them, and why they are used.

Furthermore, if any calculated values are out of the expected breathing range, they are rejected by the device 50 and never reported to the host Bluetooth™ device. Expected range is obvious to those skilled in the art. Final values reported include Breathing Frequency ("Rf"), Tidal Volume ("Tv"), Ventilation ("Ve"), Fraction of Expired Oxygen ("FeO2"), and Volume of Oxygen Consumed ("VO2").

The next step is to restart the main loop, as shown by box of numeral 300. The device 50 is configured to jump to the start of the Main Loop 248 once in a period of approximately 20 milliseconds since the start of the most recent loop has passed. This produces a sensor sample frequency of about 50 hz.

The checking of the oxygen sensor calibration 263 within the safety check 252 seen in FIG. 33C will next be discussed in greater detail. This step involves determining if the oxygen sensor calibration has gone stale. If it has gone stale, a recalibration of the oxygen sensor 122 seen in FIG. 27 is required, by switching the device 50 from State Record 264 seen in FIG. 33B back to State Calibrate 262. Possible reasons the calibration could go stale include as follows:

Mandatory 5-minute recalibration: the device 50 is configured to automatically recalibrate after the first five minutes of operation, since at this point in time the device will be closer to the operating temperature dictated by the user's breath.

Thermal shock: if temperature changes at a rate faster than 0.2 Celsius per minute, the oxygen sensor temperature compensation algorithm experiences hysteresis. Recalibrating during and five minutes after thermal shock decreases this error.

Absolute pressure or temperature have drifted by a substantial amount: environmental correction algorithms for the oxygen sensor 122 seen in FIG. 27 are based on drift since a zero-point defined at the time of oxygen sensor calibration, so compensation error grows as the drift grows. The device 50 is configured to inhibit the drift from getting too big by recalibrating.

The further particulars of sampling the air, processing resulting sensor signals, and calculating oxygen-consumption rates and the like therefrom is described in detail International Patent Application Publication No. WO 2017/177340 A1 to O'Brien et al., the disclosure of which is incorporated herein by reference.

Figure 34:
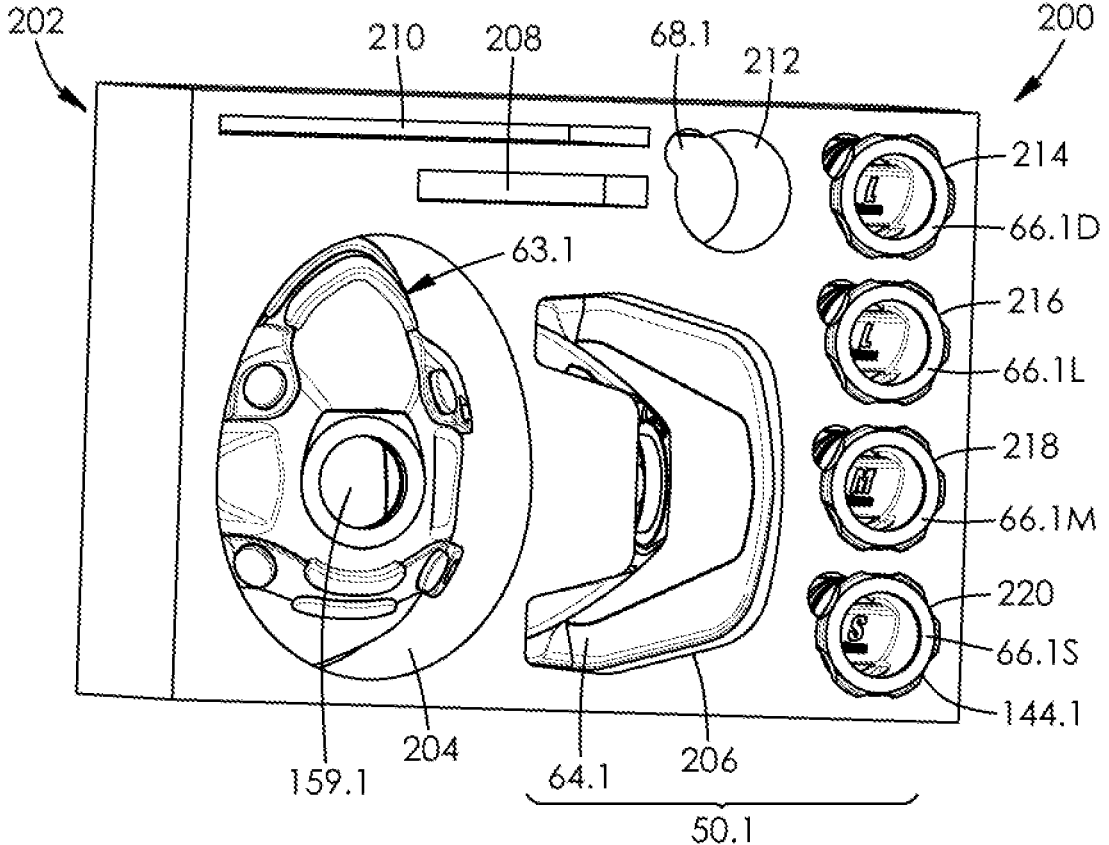
FIG. 34 is a top perspective view of a kit comprising a face mask and a ventilation measuring device according to a second embodiment, the device including the sensor assembly of FIG. 3 and a plurality of deflector assemblies each shaped to selectively couple to the face mask and sensor assembly.
Figure 36:
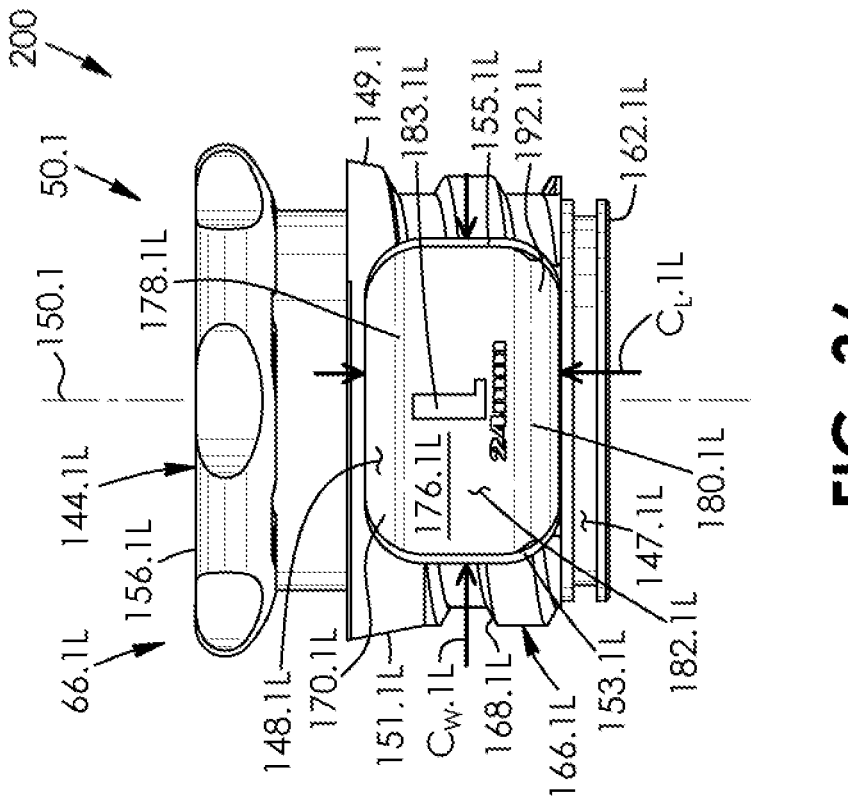
FIG. 36 is a bottom plan view of a high-flow rate one of the deflector assemblies of the kit of FIG. 34.
Figure 35:
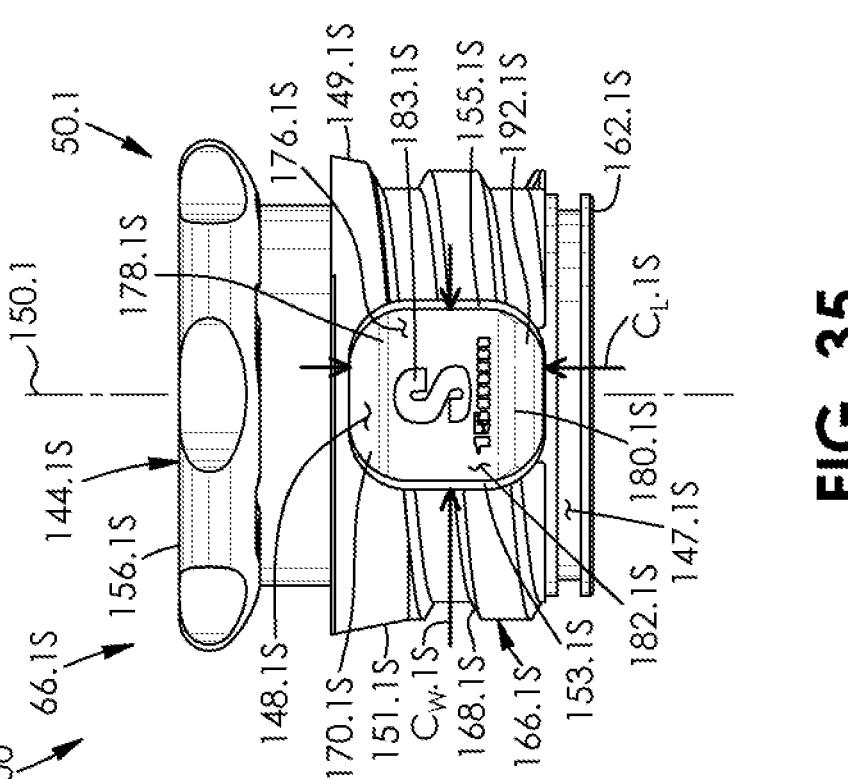
FIG. 35 is a bottom plan view of a low-flow rate one of the deflector assemblies of the kit of FIG. 34.

FIGS. 34 to 36 show a kit 200 comprising a face mask 63.1 and a ventilation measuring device 50.1 according to a second embodiment. Like parts have like numbers and function as the embodiment shown in FIGS. 1 to 33 with the addition of decimal extension "0.1". Device 50.1 is substantially the same as device 50 shown in FIGS. 1 to 33 with the following exceptions.

The kit 200 includes a housing 202 with a face mask recess 204 shaped to receive face mask 63.1, a sensor assembly recess 206 shaped to receive sensor assembly 64.1, a documentation recess 208 shaped to receive documentation (not shown), a battery recess 210 shaped to receive a battery (not shown), a filter recess 212 shaped to receive a plurality of filters 68.2 and a plurality of deflector assembly recesses 214, 216, 218 and 220. The kit further includes a plurality of deflector assemblies 66.1D, 66.1L, 66.1M and 66.1S shaped to fit within recesses 214, 216, 218 and 220, respectively. Deflector assemblies 66.1D and 66.1M are substantially the same as deflector assembly 66 seen in FIGS. 11 to 17, with deflector assembly 66.1D being a duplicate of deflector assembly 66.1M.

Referring to FIG. 35, deflector assembly 66.1S is substantially the same as deflector assembly 66 shown in FIGS. 11 to 17 for device 50, with like parts having like numbers and the addition of decimal extension "0.1S", and with the following exceptions. Rearward surface 182.1S of the deflector assembly has indicia 183.1S thereon in this example in the form a capital letter S, together with the wording "16 mm". Constriction width $C_{W.1S}$ of opening 170.1S is equal to 16 mm in this example, and is smaller than constriction width of the opening of deflector assembly 66.1M seen in FIG. 34. Referring back to FIG. 35, the constriction length $C_{L.1S}$ of deflector assembly 66.1S is substantially the same as that of deflector assembly 66.1M seen in FIG. 34 in this example. Thus, the opening 170.1S of the deflector assembly 66.1S is smaller than that of deflector assembly 66.1M. Deflector assembly 66.1S is shaped to perform measurements and acquire data when the user is resting or walking, with the assembly thus being shaped for low flow rates.

Referring to FIG. 36, deflector assembly 66.1L is substantially the same as deflector assembly 66 shown in FIGS. 11 to 17 for device 50, with like parts having like numbers and the addition of decimal extension "0.1L", and with the following exceptions. Rearward surface 182.1L of the deflector assembly has indicia 183.1L thereon in this example in the form a capital letter L together with the wording "24 mm". Constriction width $C_{W.1L}$ of opening 170.1L is equal to 24 mm in this example, is larger than constriction width of the opening of deflector assembly 66.1M seen in FIG. 34 and is larger than constriction width $C_{W.1S}$ is of the opening of deflector assembly 66.1S seen in FIG. 35. Referring back to FIG. 36, the constriction length $C_{L.1L}$ of deflector assembly 66.1L is substantially the same as that of deflector assembly 66.1M seen in FIG. 34 in this example and substantially the same as constriction length $C_{L.1S}$ of deflector assembly 66.1S seen in FIG. 35. Thus, the opening 170.1L of the deflector assembly 66.1L is larger than that of deflector assembly 66.1M and larger than that of deflector assembly 66.1S. Deflector assembly 66.1L is shaped to perform measurements and acquire data during maximal tests or high-intensity exercise while running or biking, for example, with the assembly thus being shaped for high flow rates.

Referring to FIG. 34, the sensor assembly 64.1 and deflector assemblies 66.1D, 66.1S, 66.1M and 66.1L as herein described may thus be part of a kit comprising the assembly and deflector assemblies of varied shapes. The device 50.1 so configured may thus be customizable to desired test conditions and criteria. This is advantageous because it allows for deflector assemblies 66.1D, 66.1S, 66.1M and 66.1L having different flow ranges for each size. The replaceability of each said deflector assembly, while keeping the rest of the device 50.1 the same as before, may function to reduce overall costs and improve the versatility of the device.

Figure 37:
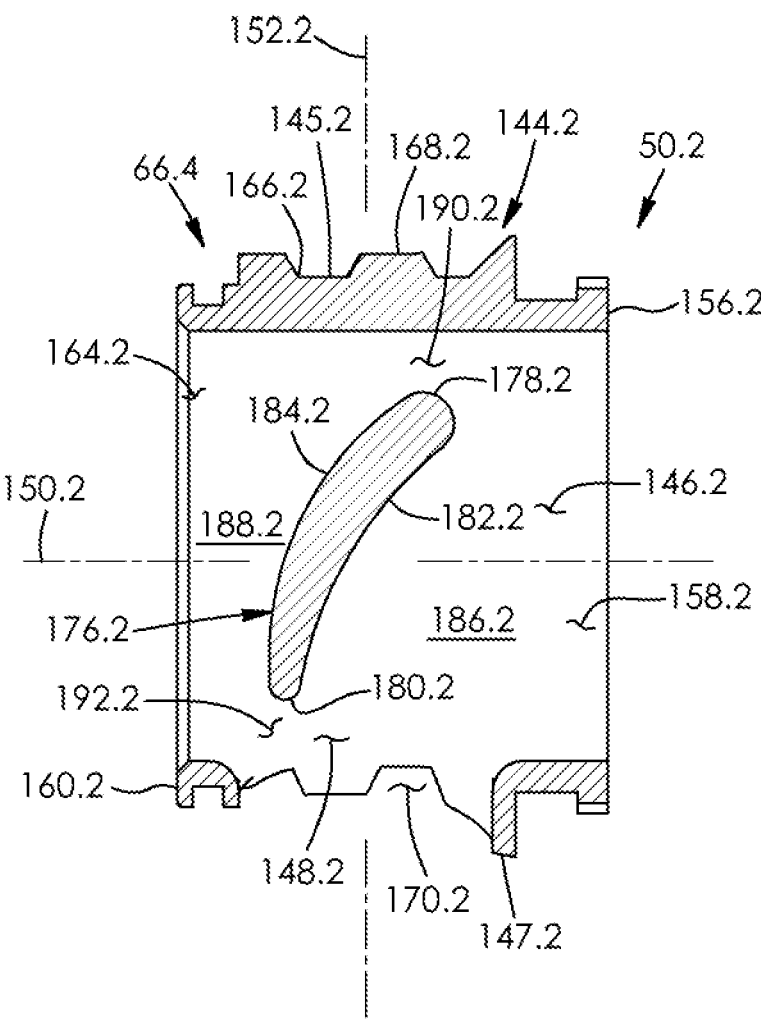
FIG. 37 is a side sectional view similar to FIG. 11 of a deflector assembly for a ventilation measuring device according to a third embodiment.

FIG. 37 shows a deflector assembly 66.2 for a ventilation measuring device 50.2 according to a third embodiment.

Like parts have like numbers and function as the embodiment shown in FIGS. 1 to 33 with decimal extension "0.2" being added thereto. Device 50.2 is substantially the same as device 50 shown in FIGS. 1 to 33 with the following exceptions.

Deflector assembly 66.2 includes a divider or deflector 176.2 that is arcuate, slanted and inclined in this example. The deflector has a first or upper peripheral portion 178.2 and a second or lower peripheral portion 180.2 that are both arcuate-shaped and convexly curved in side profile in this example.

The upper peripheral portion 178.2 of the deflector 176.2 is rearward of lower peripheral portion 180.2 of the deflector in this example and from the perspective of FIG. 37. The second or forward surface 184.2 of the deflector 176.2 is convex in this example.

Figure 38:
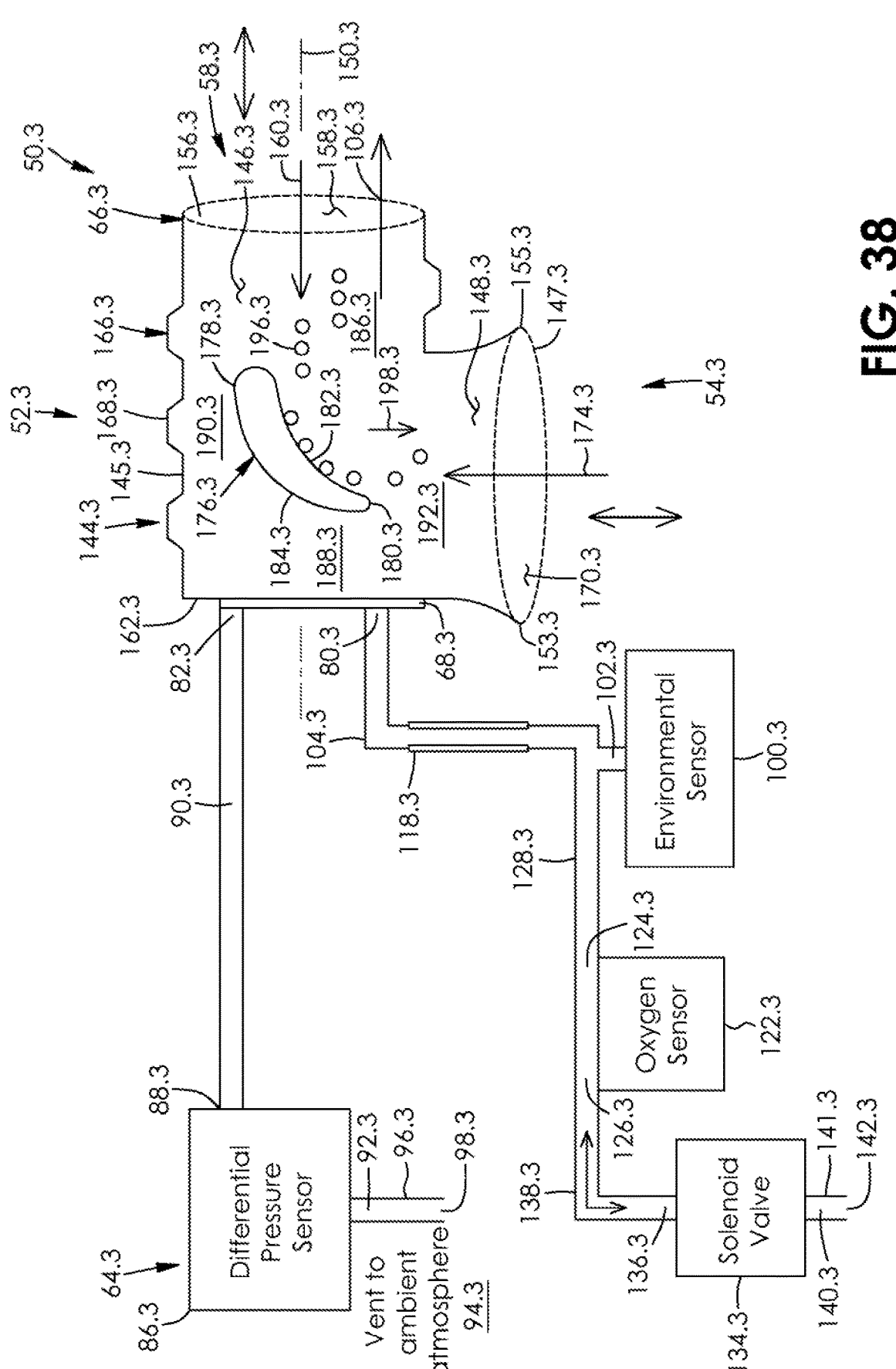
FIG. 38 is a schematic diagram of a ventilation measuring device according to a fourth embodiment.

FIG. 38 shows a deflector assembly 66.3 for a ventilation measuring device 50.3 according to a fourth embodiment. Like parts have like numbers and function as the embodiment shown in FIG. 37 with decimal extension "0.3" replacing decimal extension "0.2" and being added for like parts not previously having decimal extension. Device 50.3 is substantially the same as device 50 shown in FIGS. 1 to 33 and defector assembly 66.3 is substantially the same as deflector assembly 66.2 shown in FIG. 37 with the following exception. The upper peripheral portion 178.3 of deflector 176.3 extends in a generally planar manner to a greater extent and generally in parallel with axis 150.3, compared to upper peripheral portion 178.2 of deflector 176.2 seen in FIG. 37.

Figure 39:
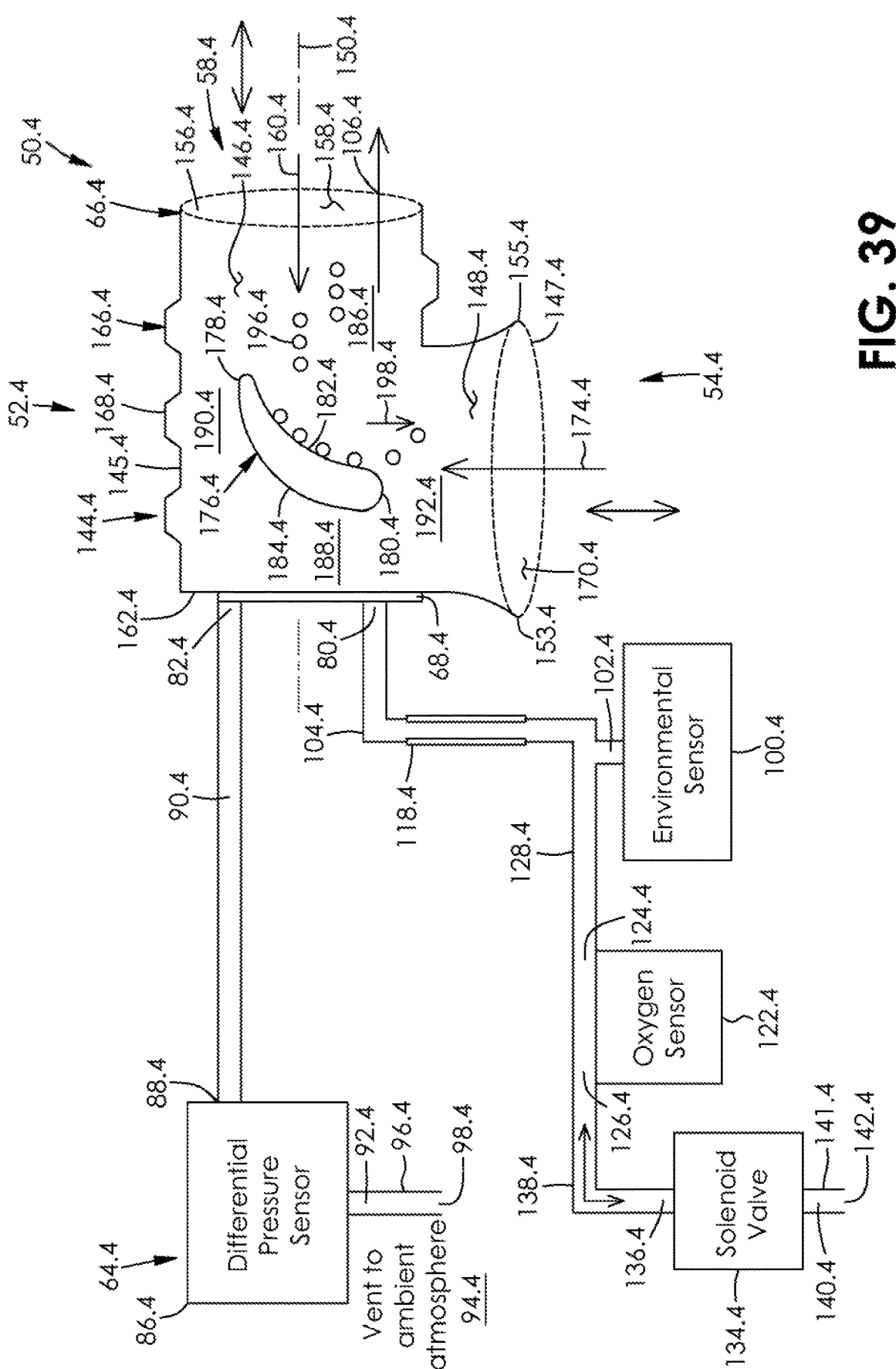
FIG. 39 is a schematic diagram of a ventilation measuring device according to a fifth embodiment.

FIG. 39 shows a ventilation measuring device 50.4 according to a fifth embodiment. Like parts have like numbers and function as the embodiment shown in FIG. 38 with decimal extension "0.4" replacing decimal extension "0.3" and being added for like parts not previously having decimal extension. Device 50.4 is substantially the same as device 50 shown in FIGS. 1 to 33 and deflector assembly 66.4 is substantially the same as deflector assembly 66.3 shown in FIG. 38 with the following exception.

Deflector 176.4 tapers from the lower peripheral portion 180.4 of the deflector to the upper peripheral portion 178.4 of the deflector in this example. The lower peripheral portion of the deflector is thus thicker than the upper peripheral portion of the deflector in this embodiment.

Figure 40:
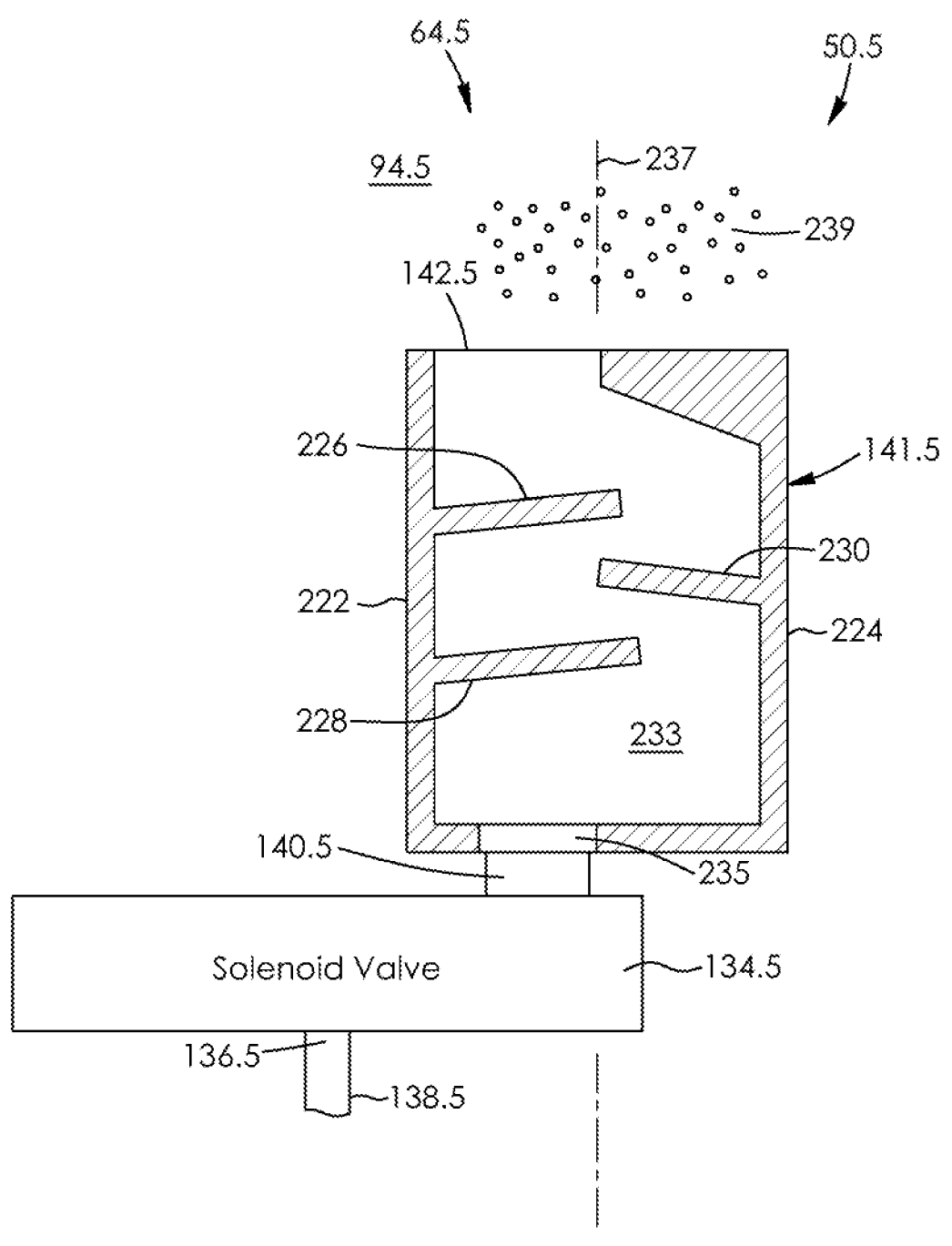
FIG. 40 is a schematic, cross-sectional view of ambient baffles of a ventilation measuring device according to a sixth embodiment.

FIG. 40 shows a conduit, in this example a baffle housing 141.5 of a ventilation measuring device 50.5 according to a sixth embodiment. Like parts have like numbers and function as the embodiment shown in FIGS. 1 to 33 with the addition of decimal extension "0.5". Device 50.5 is substantially the same as device 50 shown in FIGS. 1 to 33 with the following exceptions.

The baffle housing 141.5 has an interior 233, an inlet 235, and an open air port or outlet 142.5. The inlet and outlet are in fluid communication with the interior of the baffle housing. The outlet 142.5 is in fluid communication with the ambient air/atmosphere 94.5. The inlet 235 of the baffle housing is in fluid communication with the second port 140.5 of solenoid valve 134.5. The baffle housing 141.5 is elongate and has a longitudinal axis 237 along which the baffle housing extends. The inlet 235 and outlet 142.5 of the baffle housing are offset from the longitudinal axis of the baffle housing this example.

The baffle housing 141.5 includes one or more longitudinally-extending side walls, in this example side walls 222 and 224 which extend between the inlet 235 and outlet 142.5 thereof and which extend parallel to longitudinal axis 237 in this example. The baffle housing includes a plurality of spaced-apart baffles 226 and 228 which couple to and extend from wall 222 at regularly spaced-apart intervals in this example towards wall 224. The baffles align with and extend between inlet 235 and outlet 142.5 of the baffle housing 141.5. The baffle housing includes at least one further baffle 230 which couples to and extends from wall 224 towards wall 222. Baffle 230 is positioned between and overlaps with baffles 226 and 228 in this example. The baffles 226, 228 and 230 are rectangular in cross-section in this example. The baffles so shaped may function to inhibit moisture 239 from ambient air/atmosphere 94.5 from coming into contact with solenoid valve 134.5 and the rest of the inner components of the device 50.5.

It will be appreciated that many variations are possible within the scope of the invention described herein. It will also be understood by someone skilled in the art that many of the details provided above are by way of example only and are not intended to limit the scope of the invention which is to be determined with reference to the following claims.

What is claimed is:

1. A device for measuring a person's oxygen-consumption, the device comprising:
   a conduit having a first end through which exhalations enter the device along a first longitudinal axis thereof and having a second end through which the exhalations exit the device along a second longitudinal axis thereof angled relative to the first longitudinal axis thereof;
   a deflector positioned within the conduit and configured to direct the exhalations from the first end towards the second end of the conduit and direct inhalations from the second end to towards the first end of the conduit, the deflector aligning and intersecting with said axes, wherein the deflector is streamlined and configured to inhibit restriction to a flow of exhalations through the conduit, wherein a first flow path of the exhalations from the first end of the conduit through to the deflector is linear, with the first flow path having a proximal end adjacent the first end of the conduit and a distal end adjacent the deflector, wherein a second flow path of the exhalations from the deflector through the conduit to the second end of the conduit is linear, with the second flow path having a proximal end adjacent the deflector and a distal end adjacent the second end of the conduit, and wherein the distal end of the first flow path is near or adjacent the proximal end of the second flow path and wherein the first flow path is connected to the second flow path by a third, curved flow path defined at least in part by a curved surface of the deflector, and wherein the first, second and third flow paths are each shaped to promote a single direction of flow of said exhalations therealong; and
   an oxygen sensor sampling port positioned within the conduit, the deflector being positioned between the oxygen sensor sampling port and the first end of the conduit.

2. The device according to claim 1, wherein the device includes one or more pressure sampling ports in fluid communication with the conduit; and wherein the curved surface of the deflector is configured to deflect the exhalations passing into the first end of the conduit away from the one or more pressure sampling ports, the curved surface of the deflector facing the first end at least in part and facing the second end of the conduit at least in part.

3. The device as claimed in claim 2, wherein the deflector is configured to cause said one or more pressure sampling ports to be subject to only a portion of said exhalations passing into the first end of the conduit.

4. The device as claimed in claim 2, wherein the device is configured to measure oxygen-consumption of the person.

5. The device as claimed in claim 4, wherein the deflector is configured to primarily deflect said exhalations away from the oxygen sensor sampling port.

6. The device as claimed in claim 5, wherein the device includes a pressure sensor in communication with said one or more pressure sampling ports, with the one or more pressure sampling ports being configured to expose the pressure sensor to one or more pressure differentials, and wherein the device includes an oxygen sensor in communication with said oxygen sensor sampling port, with the oxygen sensor sampling port being configured to expose the oxygen sensor to the one or more pressure differentials.

7. The device as claimed in claim 6, further including a passage in fluid communication with the oxygen sensor and the oxygen sensor sampling port, the passage having a parabolic shape which promotes air flow towards the oxygen sensor, reducing signal response time thereby.

8. The device as claimed in claim 2 wherein the deflector is configured to direct the exhalations passing therethrough primarily through a primary chamber of the device, with a secondary reduced amount of the exhalations being directed into a secondary chamber of the device, and wherein the device further includes a first passageway positioned above the deflector and a second passageway positioned below the deflector, with the primary chamber and the secondary chamber being in fluid communication with each other via said first passageway and said second passageway.

9. The device as claimed in claim 2 wherein the conduit includes an enclosing wall that extends between the first and second ends thereof, and wherein the conduit has an opening that extends through the enclosing wall, the second end of the conduit extending from the opening towards the first end of the conduit.

10. The device as claimed in claim 9 wherein the first end of the conduit has a cross-sectional area that is larger than that of the opening of the conduit.

11. The device as claimed in claim 9 further including a filter which extends along and is positioned between the second end of the conduit and the one or more pressure sampling ports.

12. The device as claimed in claim 2 wherein the deflector is configured to inhibit external liquid from coming into contact with the one or more pressure sampling ports.

13. The device as claimed in claim 2 wherein the deflector is configured to deflect saliva passing through the first end of the conduit downwards, through the second end of the conduit and outwards from the device.

14. The device as claimed in claim 2, wherein a front end of the conduit in use is substantially closed and wherein the curved surface of the deflector is outwardly concave.

15. The device according to claim 1, wherein the deflector forms at least in part a primary channel through which the exhalations primarily flows between said ends of the conduit, wherein the deflector forms at least in part a second channel through which a reduced amount of the exhalations flow between said ends of the conduit and wherein the device includes an oxygen sensor in fluid communication with the second channel.

16. The device as claimed in claim 1 wherein the deflector is at least one of arcuate at least in part and inclined at least in part.

17. The device as claimed in claim 1, wherein the device is shaped to perform measurements and acquire data during maximal tests or high-intensity exercise.

18. The device as claimed in claim 1, wherein the conduit and the deflector are shaped for high flow rates.

19. The device as claimed in claim 1, wherein the device includes one or more pressure sampling ports in fluid communication with the conduit with the one or more pressure sampling ports having axes which extend parallel to the first longitudinal axis of the conduit.

20. The device as claimed in claim 1, wherein the conduit is shaped to enclose a substantially open space so as to facilitate passage of said exhalations substantially therethrough.

21. The device as claimed in claim 1, including a primary chamber through which the exhalations primarily flow between the ends of the conduit the primary chamber being tubular and being defined by an enclosing wall enclosing an open space, with the deflector defining a forward end of the primary chamber, with the second end of the conduit comprising an opening extending radially through said enclosing wall, and with the opening being positioned at a bottom of the conduit.

22. The device as claimed in claim 1, wherein the first flow path is longitudinally-extending, the second flow path is radially-outwardly extending and the third flow path consists of a first longitudinally-extending component and a second radially-outwardly extending component.

23. The device as claimed in claim 22, wherein the first flow path is oriented horizontally and the second flow path and the second radially-outwardly extending component of the third flow path are oriented downwards.

24. The device as claimed in claim 1, wherein the oxygen sensor sampling port is in fluid communication with a fourth flow path, the fourth flow path being exterior to the deflector.

25. A device for measuring a person's oxygen-consumption, the device comprising:
  a conduit including a tubular sidewall extending along a longitudinal axis thereof, the conduit having a proximal opening aligned with the longitudinal axis thereof and through which exhalations enter the device, the conduit having a distal opening aligned with the longitudinal axis thereof, and the conduit having a lower opening formed in said sidewall between the proximal opening and the distal opening and through which the inhalations enter the device and the exhalations exit the device;
  a distal wall via which the distal opening of the conduit is substantially closed;
  a deflector positioned in the conduit between the distal opening and the lower opening and extending laterally across the conduit between diametrically opposed sides of the sidewall, the deflector with the sidewall defining a primary chamber extending between the deflector and the proximal opening of the conduit, and the deflector with the distal wall defining a secondary chamber extending between the deflector and the distal opening of the conduit, the deflector having a first surface shaped to direct the inhalations from the lower opening to the proximal opening of the conduit and shaped to direct the exhalations from the proximal opening to the lower opening of the conduit, the deflector including an upper portion which defines with the sidewall a first passageway through which a portion of the exhalations pass from the primary chamber to the secondary chamber, and the deflector including a lower portion which defines with the sidewall a second passageway through which the portion of the exhalations pass from the secondary chamber to the lower opening; and
  an oxygen sensor sampling port in fluid communication with the secondary chamber via the distal opening of the conduit.

26. The device as claimed in claim 25, wherein the secondary chamber is cylindrical in shape.

27. The device as claimed in claim 25, wherein the first passageway and the second passageway are each a circular segment in cross-section.

28. A device for measuring a person's ventilation, the device comprising:
  a tubular conduit having a first open end, a second end spaced-apart from the first open end, a longitudinal axis which extends between the ends thereof, a bottom, and an opening between the ends thereof and extending through the bottom thereof, the conduit including an enclosing wall that extends between the ends thereof, with the opening of the conduit extending through the enclosing wall, and the conduit including an exhaled-air receiving portion and an inhaled-air receiving portion, with the exhaled-air receiving portion of the conduit extending from the first open end towards the opening, and the inhaled-air receiving portion of the conduit extending from the opening towards the first open end of the conduit;
  one or more oxygen sensor sampling ports, the second end of the conduit aligning with the one or more oxygen sensor sampling ports and the one or more oxygen sensor sampling ports being in fluid communication with the conduit; and
  a deflector positioned within the conduit between the second end and the opening of the conduit and configured to deflect air exhaled into the exhaled-air receiving portion of the conduit away from the one or more oxygen sensor sampling ports, the deflector being a triangular prism in shape.

29. The device as claimed in claim 28, wherein the deflector directs air passing therethrough primarily through a primary chamber of the device, with a secondary reduced amount of said air being directed into a secondary chamber of the device, wherein the one or more oxygen sensor sampling ports are in fluid communication with the secondary chamber, wherein the secondary chamber is in fluid communication with the primary chamber via a first passageway which is aligned with the exhaled-air receiving portion of the conduit and positioned above the deflector, and wherein the secondary chamber is in fluid communication with the primary chamber via a second passageway which is aligned with the inhaled-air receiving portion of the conduit and positioned below the deflector.

* * * * *